United States Patent [19]

Brocia

[11] Patent Number: 5,770,355
[45] Date of Patent: Jun. 23, 1998

[54] HEART DISEASE TEST KIT AND METHOD OF DETERMINING A HEART DISEASE RISK FACTOR AND EFFICACY OF A TREATMENT FOR HEART DISEASE

[76] Inventor: Robert W. Brocia, 15 Moore Rd., Bronxville, N.Y. 10708

[21] Appl. No.: 490,610

[22] Filed: Jun. 15, 1995

Related U.S. Application Data

[63] Continuation-in-part of Ser. No. 148,731, Oct. 29, 1993, Pat. No. 5,585,235.

[51] Int. Cl.[6] .............................. C12Q 1/48; C12Q 1/37; C12Q 1/00; G01N 33/48
[52] U.S. Cl. .................................. 435/4; 435/15; 435/23; 435/975; 436/63; 436/71; 436/74; 436/542; 436/13; 436/149
[58] Field of Search .................................... 435/4, 15, 23, 435/975; 436/63, 71, 74, 13, 542, 149

[56] References Cited

U.S. PATENT DOCUMENTS

| | | | |
|---|---|---|---|
| 5,279,540 | 1/1994 | Davidson | 604/4 |
| 5,512,548 | 4/1996 | Kushwaha et al. | 514/12 |

*Primary Examiner*—Louise Leary

[57] ABSTRACT

There is disclosed a non-radioactive method and kit for determining a heart disease risk factor and for determining efficacy of treatment for heart disease.

36 Claims, 14 Drawing Sheets

HEART DISEASE TEST KIT AND METHOD OF DETERMINING A HEART DISEASE RISK FACTOR AND EFFICACY OF A TREATMENT FOR HEART DISEASE

CLAIMING PRIORITY UNDER 35 USC 119 AND 120

This application is a continuation-in-part application of U.S. application Ser. No. 08\148,731, filed on Oct. 29, 1993, now U.S. Pat. No. 5,585,235.

BACKGROUND

Technical Field

This invention relates generally to diagnostic kits for heart disease and methods of determining heart disease risk factors and methods of determining the efficacy of treatments for heart disease or treatments to lower the risk of heart disease. More particularly, the present invention relates to methods and kits for determining an atherosclerosis risk factor and a method and kit for determining the efficacy of a treatment regimen for abnormalities associated with proteins that demonstrate physiological activity utilizing lipids as substrates, such as two exemplary neutral lipid transfer proteins, cholesteryl ester transfer protein (CETP) and microsomal transfer protein (MTP, also known as the triglyceride transfer protein).

Enzymes are highly specialized proteins that possess physiological activity. Enzymes are known to act as catalysts, facilitating the formation of products from reactants in carefully controlled steps. The role of the enzyme as a catalyst is complex in that the protein enables the frail surroundings of living systems to serve as the reaction vessel to break or form chemical bonds that would otherwise require high temperature or equally harsh conditions to apply energy to the reaction. The enzymes of normally functioning systems carefully regulate reactions and prevent the upset of simultaneous metabolic pathways. The field of study, Enzymology, is generally concerned with the characterization and kinetics of enzyme systems.

Enzymology recognizes changes in enzyme activity with respect to activation and inhibition of the protein and teaches the concepts of substrate inhibition or substrate activation. Substrate inhibition occurs when an enzyme that is breaking or forming chemical bonds to make product from substrates is inhibited due to the effect of high substrate concentration. Typically, in properly functioning metabolic processes enzyme activity is inhibited by the build up of products of the enzyme's action. The products may be passed off to another enzyme of a simultaneous metabolic pathways as a reactant or a substrate of a continuous path of metabolic activity. The depletion of the system's first enzyme's products by the second enzyme allows the first enzyme to resume production.

Further, it is understood that among factors modulating the activity of an enzyme is included the conformation or "shape" of the protein. The conformation is a result of the enzyme's component amino acids, linked together in a long chain, and repulsive or attractive forces mutually or in response to the surroundings. All proteins are made up of many amino acids linked together to collectively form a long "polypeptide". The component amino acids each have characteristic properties of both a chemical and physical nature. For example, some amino acids will dissolve in water and some will not dissolve in water. The properties of a protein's component amino acids have an effect on the whole protein. For example, the amino acids that will not dissolve in water may create hydrophobic pockets when the protein is placed in water. The pockets are the result of the insoluble amino acids repulsion to water combined with the soluble amino acids mingling with water together with the fact that they are tethered in chain by covalent chemical bonds. This creates a dynamic folding effect and if many non-water soluble amino acids are at one end of the protein, and similarly many water soluble amino acids are at the opposite end of the protein, in an aqueous environment the protein will coil up or "fold" so the non soluble amino acids are tightly clumped together in the middle of a stringy mass and all water molecules are squeezed out so the center of the mass may be dry while the stringy mass becomes wet as the outer parts are examined. The folded polypeptide "string" demonstrates a particular shape or conformation of the enzyme. The shape of enzymes contribute to the substrate specificity of enzymes producing the "lock-and-key" relationship between the substrate molecule and a specific area on the enzyme known as the active site.

Enzymes are inhibited by certain chemical compounds. In particular, some drugs are useful in medicine as treatments for enzyme abnormalities because they can inhibit the catalytic activity of enzymes in cells. The inhibitor may "fool" the enzyme into binding to it instead of the enzyme's substrate.

Enzymes may occur in more than one conformational form within a species, in the same tissue within one animal in a species, and even within a single cell. Hence, enzymes may have different functional conformations and therefore different kinetic activity.

There are a large number of genetic disorders in which one enzyme or another is either totally ineffective or has an increased or decreased catalytic or regulatory activity. In these genetic disorders the abnormal enzyme may contain one or more incorrect amino acids in the polypeptide chain. If the incorrect amino acid(s) affects the enzyme's conformational state, it may affect the enzyme's activity. The incorrect amino acid(s) may be the result of a gene mutation in the DNA coding for the enzyme, an error in transcription of the enzyme, or an error in the translation of the enzyme. The genetically modified enzyme's participation in a metabolic pathway may change or completely disable the production of life sustaining components including the conformational modification of other enzyme to regulate activity. The animal having this alteration is at risk for severe metabolic ramifications. These genetic alterations may indirectly affect other metabolic pathways causing abnormal activation or inactivation of an unaltered enzyme by creating an increase in the normal concentration of a substrate. The resulting change in activity may have a harmful effect on the subject animal depending on the metabolic pathway affected.

There are five major stages in enzyme synthesis: activation of amino acids, initiation of the chain, elongation, termination and release of the enzyme, and folding and processing of the enzyme. Activation involves the attachment of the 20 or so amino acids to a specific transfer RNA. Messenger RNA bearing the code for the enzyme to be made is bound to the smaller unit of a ribosome. Then the initiating amino acid attached to its tRNA follows to form an initiation complex. The tRNA of the initiating amino acid pairs with a nucleotide codon on the mRNA that signals the beginning of the enzyme's primary sequence. The enzyme polypeptide chain grows in length by the attachment of successive amino acids in a similar pairing process. A termination codon signals the completion of the polypeptide chain and the enzyme is released. The released enzyme then must become biologically active and undergo folding into its proper conformation and further removal of unneeded amino acid residues where needed.

Constitutive enzymes are those present in organisms at more or less constant amounts, and induced enzymes vary in concentration. Induced enzymes are regulated in concentration in organisms by enzyme induction and repression. Induced enzymes are present in an organism in trace amounts but increase many hundred fold or even many thousand fold when the enzyme's substrate is detected by an organism. An agent capable of inducing the synthesis of an enzyme is an inducing agent.

In contradistinction to induction, there is enzyme repression. Enzyme repression involves the "turning off" of the synthesis of an enzyme upon the addition of a compound or upon other feedback mechanisms. The repression concept is central to the principle of cell economy in that once an enzyme is no longer needed in an organism, it is no longer made.

Enzyme regulation is in the form of transcriptional control and translational control. Transcriptional control relates to the control of the rate of transcription of the genes coding for an enzyme into their corresponding mRNAs. Translational control involves the control of the rate of synthesis of the polypeptide chain from its mRNA template. There are also regulatory genes coding for a regulatory protein called a repressor. The repressor binds to a DNA segment called an operator. Further, an inducer can bind to a repressor to release the repressor for the DNA binding site.

In some human diseases, including heritable genetic disorders, there may be a deficiency in or over production of an enzyme that leads to a phenotypic disorder. Phenotypic disorders may include obesity, coronary artery lesions, and the like. In the case of excessive activity of a specific enzyme, the enzyme can be controlled by a compound to inhibit an enzyme's activity. The inhibition of an enzyme occurs at different levels. Moreover, measurements of the activity of certain enzymes in blood plasma or tissue samples, both before a treatment regimen and after a treatment regimen, are important in diagnosing disease, assessing risk factors for disease or assessing the efficacy of the treatment regimen whether by inhibition of the enzyme's activity or by dietary modifications regulating the induction of the enzyme or the enzyme's activity.

Many of these tenets of biochemistry have been applied to the screening process in the search for inhibitors of enzymes in order to artificially regulate metabolic pathways. For example, it is known that heart disease or atherosclerosis is a result of the build up and subsequent restriction of blood vessels by plaque of circulating blood to the heart muscle. It is believed a preemptive factor to plaque development is depositing or loading of the cells comprising the blood vessel lining with cholesterol in the form of cholesteryl ester. It is also believed the cholesteryl ester originates from sources that include lipoproteins, specifically the low density (LDL) and very low density (VLDL) lipoproteins. The high density lipoproteins, however, are known to be protective elements where heart disease or atherosclerosis is concerned and are desirable lipoproteins.

The medical profession utilizes several methods to minimize the exposure of that cells line the circulatory system to VLDL and LDL with the rationale that lowering the exposure of arterial walls to LDL and VLDL will lower the ability of the cells to load or uptake cholesteryl ester from these lipoproteins. Means of lowering LDL and VLDL include indirect means such as disruption of the cholesterol biosynthetic pathway that occurs within the liver cells. Drugs, such as Mevacor, inhibit HMG-Coenzyme A reductase, a key enzyme along the cellular pathway for production of cholesterol. Cholesterol is a life sustaining component necessary to maintain many basic functions such as cell membrane integrity. Cholesterol is transported throughout the circulatory system within lipoproteins in the ester form as cholesteryl ester. The ester is completely water insoluble and resides in the core of the lipoproteins. Mevacor is given in limited doses so that the pathway is not totally without output of life sustaining cholesterol but the output is partially reduced. The reduced cholesterol output from the liver results in generally a reduction of all cholesterol pools or stores. Included is the reduction of the lipoprotein cholesterol pool. Lipid transfer proteins or other proteins that utilize lipids as substrates interact with the lipoproteins to access their substrates both at the core and the surface of the lipoprotein. One lipid transfer protein, in particular a neutral lipid transfer protein, cholesteryl ester transfer protein (CETP) shuttles cholesteryl esters from HDL to VLDL and LDL. Another neutral lipid transfer protein, microsomal or triglyceride transfer protein (MTP) is believed to secrete VLDL from liver cells into the plasma.

Notwithstanding all of the advances and discoveries associated with the understanding of the biochemistry of these transfer proteins, there exists a need for non-radioactive methods and kits to simplify, facilitate, and quantify a risk factor for heat disease, and in particular atherosclerosis and other disorders involving cholesteryl ester deposits. There further exists a need for non-radioactive methods and kits for determining the efficacy of treatments affecting the activity of and abnormalities in lipid transfer protein activity in physiologic samples of CETP or MTP sources and the like.

It would be highly desirable to solve the variety of problems enumerated above facing service providers such as physicians, clinical hospital staff, laboratories and the like who assist in the diagnosis of risk factors for atherosclerosis, treatment of lipid transfer protein disorders, and, in particular, treatment of CETP and MTP related disorders such as coronary artery lesions.

It is an object of the present invention to provide hundreds of millions of individuals who are at risk of developing atherosclerosis either as a result of genetic factors, diet, or the like with a simple non-radioactive diagnostic tool and method for the diagnosis of risk factors for atherosclerosis, and the efficacy of treatments of lipid transfer protein, e.g. neutral lipid transfer protein, related disorders such as coronary artery lesions. The present invention targets this group of hundreds of millions of individuals worldwide by providing a method and kit for determining a heart disease risk factor, namely, abnormal activity of neutral lipid transfer protein, and a method and kit for determining the efficacy of a treatment for abnormal activity of neutral lipid transfer protein.

SUMMARY OF THE INVENTION

These and other objects of the present invention are achieved in a method of simplifying the determination and quantification of a lipid transfer protein's role as a coronary heart disease risk factor that includes the steps of obtaining a sample of cellular extract, cellular homogenate, blood or plasma from a mammal or other source of lipid transfer protein, optionally, incubating at a specified temperature for an effective time period the sample in a non-radioactive lipid transfer protein assay to obtain an incubated sample, measuring the lipid transfer protein activity of the incubated sample to determine a lipid transfer protein activity value and, comparing the sample's lipid transfer protein activity value to a predetermined standard value. Exemplary, lipid transfer proteins include neutral lipid transfer proteins. In a variant, the method further comprises the steps of adding a prepared stable emulsion of self-quenched fluorescent lipid to act as a lipid donor. Exemplary, self-quenching fluorescent lipids include a sonicated or microfluidized particle that optionally comprises at least an apolipoprotein or a charged emulsifier added to a buffer to form a buffered solution.

The method further comprises the steps of adding a lipid rich particle, such as VLDL, to the buffered solution to accept the transfer of the fluorescent lipid, adding the source of lipid transfer protein to the buffered solution, and reading a fluorescence of the buffered solution. In yet a further variant, the lipid transfer protein assay is a neutral lipid transfer protein assay commercially available from Diagnescent Technologies, Inc. of Yonkers, N.Y. The method also optionally utilizes a non-radioactive CETP plasma assay that has a sensitivity envelope which is in the range of 0.1 $\mu$l to greater than 3.0 $\mu$l of plasma. The method also optionally includes a non-radioactive MTP assay that has a sensitivity envelope that allows the use of cellular homogenate.

The methods utilize various sources of lipid transfer protein and include sources having a naturally occurring concentration of CETP including blood and its constituents, e.g. plasma. Normal human plasma and some animal plasma have naturally occurring concentrations of neutral lipid transfer proteins including CETP. Preferably, 0.1 $\mu$l to greater than 3.0 $\mu$l of plasma are used in the methods described herein. Effective time periods include time periods in the range of seconds, for partially purified protein, to hours or even days for plasma samples or cellular media. The preferred predetermined standard values are within a range of 1 to 100 picomoles of fluorescent cholesteryl ester transferred per 3 hours of incubation per microliter of plasma which are referred to as Diagnostic Value Units. For example, a result from a sample of plasma at 30 pmoles of fluorescent cholesteryl ester transferred in 3 hours of incubation per using one microliter of plasma as the CETP source is 30 Diagnostic Value Units.

A non-radioactive method of facilitating and simplifying the screening for defects affecting the activity of the gene coding for a lipid transfer protein and kit for carrying out the method is also provided and includes the steps of obtaining a sample of naturally occurring lipid transfer protein, incubating for an effective time period the sample in a non-radioactive lipid transfer protein assay to obtain an incubated sample, measuring the protein's activity of the incubated sample to determine a CETP activity value, and comparing the sample's CETP activity value to a predetermined standard value derived from normal patient plasma. Defects in the gene include defects affecting the primary amino acid composition of CETP, the secondary structure of the lipid transfer protein, the conformational structure of the protein or a combination thereof.

It is a further object to provide a non-radioactive method of facilitating, simplifying and quantifying a determination of the efficacy of a compound inhibiting CETP or other lipid transfer protein activity and kit and screen for carrying out the method. The method comprises the steps of obtaining a sample of plasma from a mammal having a source of CETP or other lipid transfer protein, incubating for an effective time period the sample in a non-radioactive CETP or other lipid transfer protein assay to obtain an incubated sample, measuring the CETP or other lipid transfer protein activity of the incubated sample to determine a CETP or other lipid transfer protein activity value and, comparing the sample's CETP or other lipid transfer protein activity value to a predetermined standard value. The method and kit are used to determine the efficacy of a treatment designed to affect CETP or other lipid transfer protein activity. The treatment includes a compound that inhibits the transcription of a gene coding for CETP or other lipid transfer protein, a compound that inhibits the translation of a gene coding for CETP or other lipid transfer protein, a compound that is a treatment for atherosclerosis, a modification in diet affecting CETP or other lipid transfer protein activity, atherogenic diet modifications affecting CETP or other lipid transfer protein activity or combination thereof.

It is a further object to provide a non-radioactive method of facilitating, simplifying and quantifying a determination of the efficacy of a compound inhibiting MTP activity and kit for carrying out the method. The method comprises the steps of obtaining a sample from a mammal or non-mammal such as a genetically altered yeast or other cell having a source of MTP, incubating for an effective time period the sample in a non-radioactive MTP assay to obtain an incubated sample, measuring the MTP lipid transfer protein activity of the incubated sample to determine a MTP activity value and, comparing the sample's MTP activity value to a predetermined standard value or a value of a similar sample before treatment with an inhibitor. The method and kit are used to determine the efficacy of a treatment designed to affect MTP activity. The treatment includes a compound that inhibits the transcription of a gene coding for MTP, a compound that inhibits the translation of a gene coding for MTP, a compound that is a treatment for atherosclerosis, a modification in diet affecting MTP activity, atherogenic diet modifications affecting MTP activity or combination thereof.

It is yet a further object to provide a non-radioactive kit and method of determining an HDL/LDL risk ratio or a risk factor for obesity or diabetes. The method includes the steps of obtaining a patient's plasma, incubating a sample of the plasma for an effective time period in a non-radioactive CETP assay to obtain an incubated CETP source, placing the incubated CETP source in a measurement instrument in which a value representing CETP activity for the source is obtained and, comparing the value representing CETP activity with a pre-determined range. The pre-determined range includes regions of low CETP activity, moderate CETP activity, and high CETP activity derived from patients with high and low risk of heart disease according to their HDL/LDL cholesterol ratio.

It is yet another object to provide a kit and non-radioactive method of determining the efficacy of a treatment for a medical condition associated with abnormal levels of CETP or other lipid transfer protein comprising the steps of obtaining a CETP source from a donor, incubating for an effective time period the CETP source in a non-radioactive CETP assay to obtain an incubated CETP source, placing the incubated CETP source in a measurement instrument in which a value representing CETP activity for the source is obtained and, comparing the value representing CETP activity with a pre-determined range. The medical conditions include hypoalphalipoproteinemia, abnormal and normal ratios of plasma apolipoprotein A-I to apolipoprotein B.

It is yet another object to provide a kit and non-radioactive method of determining the efficacy of a treatment for a medical condition associated with abnormal levels of MTP comprising the steps of obtaining a MTP source from a donor, incubating for an effective time period the MTP source in a non-radioactive MTP assay to obtain an incubated MTP source, placing the incubated MTP source in a measurement instrument in which a value representing MTP activity for the source is obtained and, comparing the value representing MTP activity with a pre-determined range. The medical conditions include abetalipoproteinema, abnormal and normal ratios of plasma apolipoprotein A-I to apolipoprotein B. The methods described herein can also be used with other lipid transfer proteins, including but not limited to neutral lipid transfer proteins. These and other objects will become apparent in the course of a detailed description of the invention.

DETAILED DESCRIPTION OF THE PREFERRED EMBODIMENTS

Figure 1:
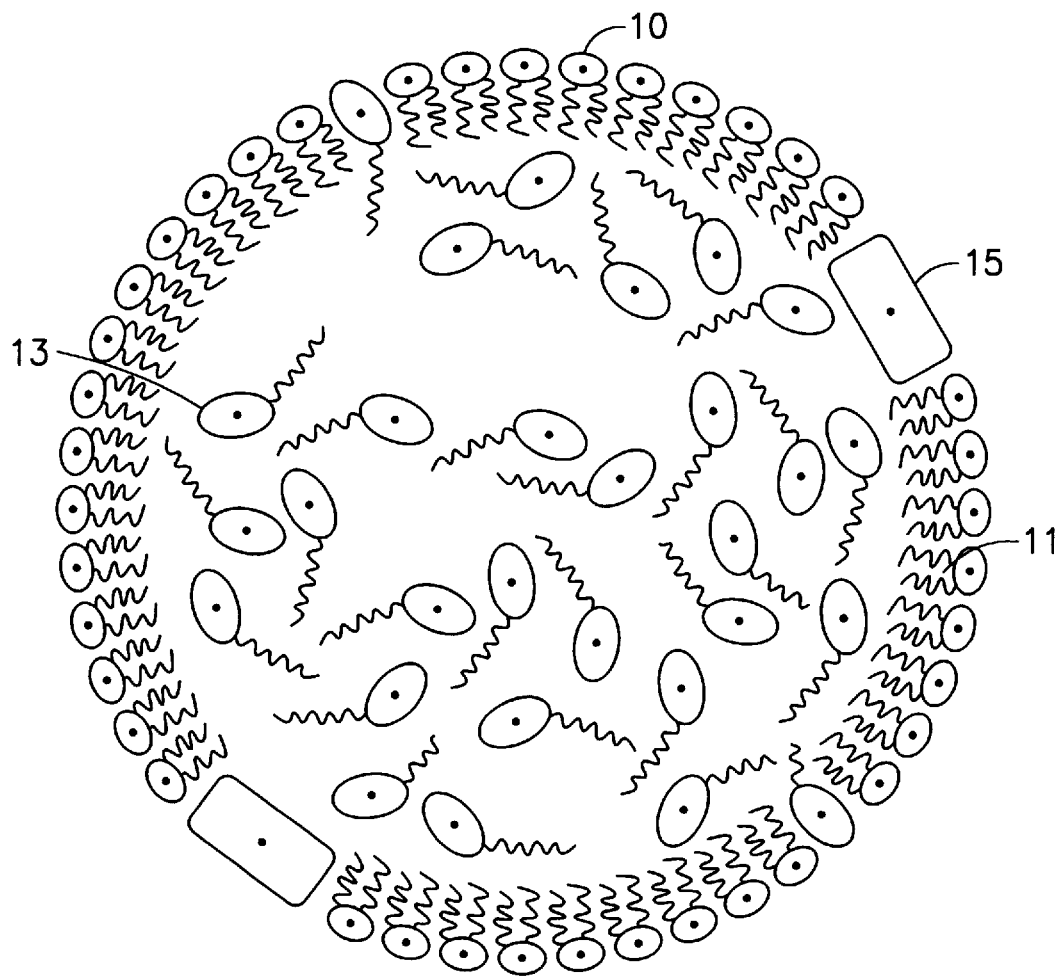
FIG. 1 is an exemplary donor particle utilized in the kits apparatus and methods described herein.

By way of example, the methods and kits described herein are used by health care professionals, laboratories, clinics, hospitals, research and development departments of corporations, universities, researchers, and other users for determining a risk factor for atherosclerosis, determining the efficacy of treatments (including drugs, naturally occurring compounds, and dietary modifications) affecting the activity or expression of lipid transfer proteins including by way of example, CETP and/or MTP, determining in-vitro and in-vivo compounds that inhibit CETP and for determining genetic abnormalities associated with disorders of lipid transfer protein activity.

Lipid transfer proteins are unique in that they include a group of proteins that, unlike other enzymes, possess no chemical bond breaking or catalytic activity. However, they do actively associate with lipids and demonstrate physiological activity and perform metabolic functions with respect to lipid transport. The lipid transfer proteins MTP and CETP are proteins that utilize lipids as substrates including, for example, neutral lipids, phopholipids, and charged lipids. CETP is a protein that may be isolated from the plasma of some organisms or other CETP source, including human CETP sources such as plasma. Similarly, MTP is a protein with activity in the liver, in intestinal cells and other sources. Neutral lipid transfer protein ligands include two neutrally charged or non-polar lipids, namely, cholesteryl esters ("CE") and triglycerides ("TG").

These hydrophobic, neutral lipids are present within the core of the lipoprotein particles, and include but are not limited to: high density lipoproteins ("HDL"), low density lipoproteins ("LDL") and very low density lipoproteins ("VLDL"). Most lipoproteins are freely circulating in the plasma of an organism. The CETP transfers the two neutral lipids CE and TG from one lipoprotein particle, the donor, to another lipoprotein molecule, the acceptor. MTP is a protein that is naturally occurring in certain organisms, present in a liver or intestinal cell or expressed by a genetically engineered yeast cell or a liver cell line, will also transfer neutral lipids among donor and acceptor particles.

As such, lipid transfer proteins do not demonstrate typical catalytic activity. In some animal and human diseases, especially heritable genetic disorders, there may be a deficiency in or over production of lipid transfer protein activity by increased protein mass or spill over from other metabolic processes that leads to a phenotypic disorder. Exemplary phenotypic disorders include extremely high levels of HDL cholesterol in animals and humans exhibiting CETP deficiency, hyperalphalipoproteinemia associated with a genetic deficiency of plasma CETP, obesity or diabetes associated with high levels of CETP activity, low levels of HDL in patients exhibiting high CETP activity, accelerated development of atheroshclerotic lesions in organisms expressing CETP genes, and hypertriglyceridemia and low HDL cholesterol phenotypes associated with transgenic expression of CETP genes. Exemplary phenotypic disorders of MTP deficiency include abetalipoproteinemia which is characterized by the absence of apolipoprotein B containing lipoproteins.

Typically, enzymes that break or make chemical bonds are active when the substrate is present, and the activity lessens as product is formed even though there may be more reactant available. Counter intuitively, substrate inhibition is also a modulating factor when catalytic enzymes are involved in a reaction. The elevated reactant concentration inhibits the protein activity. Lipid transfer proteins, however, are different in that their activity is controlled by the physical state of the lipid substrates to be transferred. There are several liquid crystalline phases of lipids as well as liquid and crystalline states. The physical states of the lipids are characterized by the ordering of the molecules. For example the ordering may include configurations where the lipid molecules are arranged from head to tail, head to head, or are completely random or not arranged. The different states are demonstrated in vitro by varying the temperature of the lipid. In vivo, however, the lipids may be at constant temperature and, in this case, the lipid is included in a mixture of two or more lipids. The lipid transfer proteins effectively change the energetic state of the mixture by acting upon the components, which effectively modulates the activity of the other enzymes by altering the physical state of another enzymes substrate. For example, lipase is an enzyme that hydrolyzes triglyceride (TG), the TG may be in the core of a newly form VLDL particle. Also present in the core of the VLDL is cholesteryl ester (CE). The core of the VLDL may be fluid if a unsaturated form of triglyceride were the predominant TG component and even though there is a CE component that would normally at be crystalline at the example VLDL's temperature, the TG acts as a solvent for the CE. As the lipase hydrolyses the TG, the CE begins to approach a more crystalline phase.

This is analogous to dissolving salt in water and slowly boiling off the water. The water is the solvent for the salt as the TG is the solvent for CE. In the salt water analogy, the salt begins to crystallize out of the water as the water is evaporated, much like the lipase is removing the TG of VLDL, although the enzyme is working at constant temperature. If the CE becomes crystalline in the core of the VLDL the activity of CETP, which may be attempting to deposit CE, is now affected by the physical state of the substrate already in the core. The same interdependency between other lipid active proteins occurs, such as phospholipid transfer proteins. A patient with an altered lipase activity may be incorrectly diagnosed as having a distinct type of CETP activity.

The core of a lipoprotein comprises a hydrophobic environment where the neutral lipids remain isolated from the aqueous plasma environment enveloped by polar phospholipids. In the case of HDL the apo AI is associated with the phospholipid and slightly associated with the outer most portion of the core neutral lipids. LDL and its precursor, VLDL, are large lipoproteins with an apolipoprotein, apo B. The apo B is unique because it is heavily associated with the core lipids and actually passes through the spherical lipoprotein. Enzymes associated with lipoproteins demonstrate activity unlike the typical catalytic enzymes. If the energetic or entropic state of the core of the lipoprotein or lipid transfer protein affected molecule changes, the activity of the enzymes is affected, the activity of the lipid transfer proteins interacting with the lipoprotein is modulated. The energetic state of the core of a lipoprotein or molecule affected, by or interacting with lipid transfer protein is modulated by compounds that dissolve or partition themselves into the core or other portion of the lipoprotein or molecule affected by interacting with lipid transfer protein. An exemplary, compounds that partition itself into the core of a lipoprotein or other portion thereof is Probucol® commercially available from Marion Merrill Dow, Inc. of Kansas City, Mo. Probucol® and derivatives thereof is a cholesterol lowering drug, that changes the energetic state of the core of the lipoprotein and therefore affects lipid transfer protein activity. The present invention uses Probucol® and derivatives thereof as a treatment to affect CETP activity. Other compounds of the same class as Probucol® are also contemplated as a treatment to affect CETP activity.

Lipid metabolism, with respect to lipoproteins, as disclosed herein is presented in terms of the purest form of the example. This is in terms of the neutral lipids and neutral lipid transfer proteins because other lipid active lipid transfer proteins may demonstrate the conventional catalytic activity, such as lipase, and still unconventionally derive activation and inhibition similar to the neutral lipid transfer proteins, i.e. by modulating the physical state of the lipid substrates.

Neutral lipid transfer protein activity is modulated by the entropic state of the lipid substrates. The entropic state of the lipids interacting with lipid transfer protein is modulated by the solvency status of the lipoprotein core. For example, a VLDL particle comprised of a fluid core of both triglycerides and cholesteryl esters is associated with exemplary lipid active enzymes such as lipase, CETP and phospholipid transfer protein. Triglyceride plays the part of the solvent dissolving the cholesteryl ester from crystalline state to a fluid variable energetic liquid crystalline. The higher the degree of saturation of the triglyceride molecule, the less cholesteryl ester it dissolves at constant temperature. VLDL is associated with other apo proteins than apo B protein that are lost as VLDL becomes LDL. The down sizing of VLDL to LDL is a result of forces associated with liquid crystalline to crystalline phase changes of the core lipids. The system is further augmented by the hydraulic forces of liquid crystal and crystal formation applying force upon the proteins associated with the lipids. For example, VLDL's loss of proteins may occur from dissociation of the proteins as the core undergoes physical change, however, apo B undergoes conformational change as core hydraulic forces apply stress to the portion of the protein that bisects the lipoprotein. The metabolism of VLDL to LDL and conformational change of apo B, in turn, modulates the LDL binding to the LDL receptor on the liver.

Lipid transfer protein activity is measured through the use of a stable emulsion prepared so the lipid transfer protein may interact with the synthetic emulsion as it does with physiological lipoproteins. The method is a non-radioactive method of simplifying the screening for defects of the gene coding for a lipid transfer protein, e.g. neutral lipid transfer, affecting the activity or expression of lipid transfer protein e.g. neutral lipid transfer, comprising the steps of obtaining a source or sample of lipid transfer protein, e.g. neutral lipid transfer, from a mammal or cell expressing the protein including yeast. By way of example, the lipid transfer protein is CETP or MTP. The source of CETP includes natural sources of CETP including whole blood, plasma, liver, small intestine, spleen, adrenal gland, adipose tissue, extracts therefrom, and combinations of extracts thereof. The source of MTP includes natural sources of MTP including liver, intestine or cell expressing MTP. A source of neutral lipid transfer protein also includes recombinant organisms, and extracts therefrom, having a gene coding for neutral lipid transfer protein or variant thereof, incorporated into the organism's genome with expression thereof. Recombinant organisms include, by way of example, transgenic mice, and also other transgenic organisms.

The method further includes the step of incubating for an effective time period the sample in a non-radioactive lipid transfer protein assay to obtain an incubated sample. Exemplary incubation time periods include periods in the range of hours to seconds, depending on the purity or specific activity of the lipid transfer protein. As used herein, incubation can also occur at room temperature. Non-radioactive lipid transfer protein assays include assays commercially available from Diagnostic Technologies, Inc. of Yonkers, N.Y. under the trade name Diagnostic™ kits. By way of further example, non-radioactive lipid transfer protein assays also include the kits, reagents and methods of using same described below.

The method further includes the step of measuring the lipid transfer protein activity of the incubated sample to determine a transfer protein activity value, and comparing the sample's lipid transfer protein activity value to a predetermined standard value. CETP activity values include values in the range of 0, for the CETP deficient individuals to 100 Diagnostic Value Units for transgenic animals, animals or cell lines over expressing CETP. The term Diagnostic Value Unit as used herein refers to picomoles of fluorescent cholesteryl ester transferred per 3 hours per microliter of plasma or other source of protein in physiological concentration. Predetermined standard values include values in the range of 0 to 100 Diagnostic units and include low levels of CETP activity, moderate levels of CETP activity, and high levels of CETP activity. Standard statistical methods are used to calculate mean and median values, varying quartile values, and other statistically significant bell curve distributions of CETP activity for particular age groups within a population, particular phenotypes within a population, or other standard sub-categorize of a population.

The method further includes the step of measuring the lipid transfer protein, e.g. neutral lipid transfer protein, activity of a patient's plasma to determine a HDL/LDL heart disease risk ratio value, and comparing the value to a predetermined standard value. For example, the activity of CETP and derivatives thereof in a patient's plasma transfers HDL cholesteryl ester to LDL and therefore yields information concerning a patient plasma lipid profile. Specifically, the ratio of HDL/LDL cholesterol is reflected and dependent upon the patient's plasma CETP activity.

A non-radioactive method of determining the efficacy of a compound inhibiting a lipid transfer protein, including but not limited to, CETP activity or MTP activity is further provided herein. In the case of excessive activity of neutral lipid transfer protein, neutral lipid transfer protein activity can be controlled by a compound that inhibits the respective transfer protein's activity. The inhibition of neutral lipid transfer protein occurs at different levels. The activity of proteins or lipid transfer proteins utilizing lipids as substrates, such as neutral lipid transfer proteins, depends upon the protein's conformation and the physical state of the lipid substrate. For example, if neutral lipid transfer protein is boiled, treated with acid, or otherwise experiences a conformational change as occurs with denaturalization, the neutral lipid transfer protein loses activity. The conformation of the neutral lipid transfer protein contributes to the substrate specificity of the protein and produces the "lock-and-key" relationship between the molecule it interacts with and a specific area on the lipid transfer protein known as the CETP active site and MTP active site.

Neutral lipid transfer proteins as functional three dimensional molecules are inhibited by certain chemical compounds. At one level, neutral lipid transfer proteins are inhibited by compounds that interfere with the "lock-and-key" relationship between the natural physiological "substrates" of the lipid transfer proteins and the lipid transfer proteins' respective active site(s). Two types of neutral lipid transfer protein inhibitors include irreversible and reversible inhibitors. Irreversible inhibitors combine with and/or destroy the functional group of the neutral lipid transfer protein lipid transfer protein that is necessary for the lipid transfer proteins' respective catalytic activity. Exemplary, reversible inhibition of neutral lipid transfer protein includes delipidating the protein, and restoring activity with phospholipid enrichment. Reversible inhibition also occurs when donor or acceptor lipid particle contains neutral lipid at a particular liquid crystalline physical state. Exemplary inhibitors of neutral lipid transfer protein include a class of compounds known as quinones, such as 1,4-benzoquinone, and derivatives thereof There are five major stages in lipid transfer protein synthesis. By way of example, CETP and/or MTP lipid transfer protein synthesis involves activation of amino acids, initiation of the CETP and/or MTP polypeptide chain, elongation of the neutral lipid transfer protein polypeptide chain, termination and release of the neutral lipid transfer protein lipid transfer protein, and folding and processing of the neutral lipid transfer protein lipid transfer protein. Activation involves the attachment of the 20 or so amino acids to a specific transfer RNA; messenger RNA bearing the code for the CETP and/or MTP lipid transfer protein to be made is bound to the smaller unit of a ribosome. Then the initiating amino acid is attached to its tRNA and forms an initiation complex. The tRNA of the initiating amino acid pairs with a nucleotide codon on the mRNA that signals the beginning of the lipid transfer protein primary sequence. The CETP and/or MTP lipid transfer protein chain grows in length by the attachment of successive amino acids in a similar pairing process. A termination codon signals the completion of the CETP and/or MTP polypeptide chain and the CETP and/or MTP lipid transfer protein is released. The released CETP and/or MTP lipid transfer protein then becomes biologically active and undergoes folding into its respective proper tertiary conformation, and also further processing consisting of removal of unneeded amino acid residues where necessary.

The method and kit of the present invention facilitates and simplifies the determination of the efficacy of a compound that inhibits the transcription/translation of a gene coding for CETP and/or MTP or other lipid transfer protein. For example, a compound that inhibits transcription/translation of a gene coding for lipid transfer protein, e.g. CETP and/or MTP, includes a segment of DNA/RNA having a complementary sequence to the gene segment coding for the respective lipid transfer protein. Complementary sequences used as inhibitors are constructed using standard genetic engineering techniques. By way of example, a segment of RNA is constructed complementary to CETP mRNA. The organism is given a treatment comprising of the complementary segment of RNA. The complementary segment of RNA base pairs with the CETP mRNA and translation of the CETP is modified. The present invention contemplates using the RNA segment complementary to the CETP mRNA is a treatment for atherosclerosis. The methods and kits herein are used to determine the efficacy of the complementary RNA segments as inhibitors of CETP translation/transcription.

Constitutive lipid transfer proteins are those present in organisms at more or less constant amounts, and induced lipid transfer proteins vary in concentration. Induced lipid transfer proteins are regulated in concentration in organisms by lipid transfer protein induction and repression. Induced lipid transfer proteins are present in an organism in trace amounts but increase a thousand fold when the lipid transfer proteins'substrate is detected by the organism. An agent capable of inducing the synthesis of an lipid transfer protein is an inducing agent. CETP and MTP are proteins whose genes may be subject to dietary regulation and diet induced changes in lipid metabolism. Atherogenic diets, e.g. those high in cholesterol, having inducing agents capable of inducing the synthesis of CETP or MTP and increasing the risk associated with the formation of atherosclerotic lesions.

A dietary modification regimen is prescribed by a health care professional including a doctor, nurse, nutritionist and the like that directly affects the induction, activity, or transcription or translation of CETP, other lipid transfer protein, e.g. neutral lipid transfer protein and/or MTP. The dietary modification regimen is used as a treatment to directly or indirectly affect the activity of CETP and/or MTP. Prior to the dietary modification regimen, a baseline CETP and/or MTP value is determined for a patient using the methods and kits described herein. The patient follows the dietary modification regimen over a predetermined period of time. The baseline CETP and/or MTP value is compared to a predetermined range of values considered normal for the patient's phenotype, age, gender, and/or genotype. Where the patient's CETP and/or MTP value is outside the norm, a treatment affecting CETP and/or MTP activity is recommended. The treatment comprises a dietary modification regimen in one variant, a compound that inhibits CETP and/or MTP activity, a compound that affects the transcription/translation of CETP and/or MTP, exercise regimen, or combination thereof. The treatment affects the induction of CETP and/or MTP. Where the treatment comprises a non-atherogenic diet regimen and/or physical exercise CETP and/or MTP activity values decrease, there is a decreased risk factor for developing atherosclerosis. After treatment, the patient returns for a follow up visit and a new CETP and/or MTP activity value is determined. Further treatment is prescribed that affects CETP activity values if needed.

A non-radioactive method and kit for determining the efficacy of atherogenic diet modifications on CETP activity is utilized. The method includes the steps of obtaining a CETP source from a patient/donor, incubating for an effective time period the CETP source in a non-radioactive CETP assay to obtain an incubated CETP source, placing the incubated CETP source in a measurement instrument in which a value representing CETP activity for the source is obtained and, comparing the value representing CETP activity with a pre-determined range.

In contradistinction to CETP/MTP induction, there is CETP/MTP repression. Repression involves the "turning off" the synthesis of the CETP and/or MTP upon the addition of a compound or upon treatment of a patient with the compound. The CETP/MTP repression concept is central to the principle of cell economy in that once high levels of CETP/MTP lipid transfer protein are no longer needed in an organism, the respective lipid transfer protein are no longer made.

CETP and/or MTP regulation is in the form of transcriptional control and translational control. Transcriptional control relates to the control of the rate of transcription of the genes coding for CETP and/or MTP into their corresponding mRNAs. Translational control involves the control of the rate of synthesis of the CETP and/or MTP polypeptide chain from its respective mRNA template. There are regulatory genes coding for regulatory proteins of CETP and/or MTP called CETP repressors and MTP repressors. The CETP repressor binds to the DNA segment coding for CETP called the CETP operator. Further, a CETP inducer can bind to a CETP repressor to release the CETP repressor from the DNA binding site. The methods and kits described herein are used to measure the efficacy of CETP represssors, MTP repressors, compounds affecting the transcription of CETP/MTP, and compounds affecting the translation of CETP/MTP.

A non-radioactive method of determining the efficacy of a compound inhibiting CETP or MTP activity in vivo is provided. The compound may inhibit the translation of the gene coding for CETP or MTP, or generally inhibits the expression of CETP or MTP. The method comprises the steps of obtaining a sample of a fluid having a source of CETP or MTP, such as plasma, in the case of CETP, or fluid extract from a liver or intestinal biopsy, in the case of MTP, from an animal model for a disease or a patient with a disease or either treated with a compound being tested for inhibitory activity of a neutral lipid transfer protein. Incubating for an effective time period the sample in a non-radioactive assay to obtain an incubated sample, measuring the CETP or MTP activity of the incubated sample to determine a activity value and, comparing the sample's CETP or MTP activity value to a control value or predetermined standard value or other value for inhibitor's of CETP.

FIG. 1 illustrates an exemplary donor particle. The stable emulsion particle 10 illustrated in FIG. 1, is prepared by sonicating about 14 micromoles of N-(7-nitrobenz-2-oxal, 3-diazol-4-yl amino ("NBD") labeled neutral lipid (CE or TG) 13, with about 13 mg of phosphatidylcholine lipid ("PC") 11, at a power output in a 550 Watt sonicator of about 40 to 50%. A temperature above the melting point of the mixture of component lipids is maintained for about 45 minutes in a buffer of that includes the following: 10 ml, 0.1M KCl/10 mM trizma-HCL, pH=8. The sonicated mixture is rapidly cooled to a temperature of about 40 degrees centigrade. Then an apolipoprotein is added, such as about 10 mg of apoA-I, 15 in about 2.5 molar urea in less than 1 ml over a time period of about 15 min. at sonication power approximately half of that used for the high temperature sonication. A self-quenching label other than NBD is also used in the kits and methods described herein.

Where a particle similar to HDL is required, the resulting emulsion is ultra-centrifuged at a density of about 1.063 g/ml with 1.21 g/ml underlay and a 1.006 g/ml overlay, other densities may be utilized. The HDL density class particle is harvested form the 1.063 g/ml middle zone. The particle utilizes the apolipoprotein for stabilization, similar to physiological conditions. Stabilization of the fluorescent donor is also accomplished with synthetic, amino acid peptides or a suitable protein such as casein.

Figure 2:
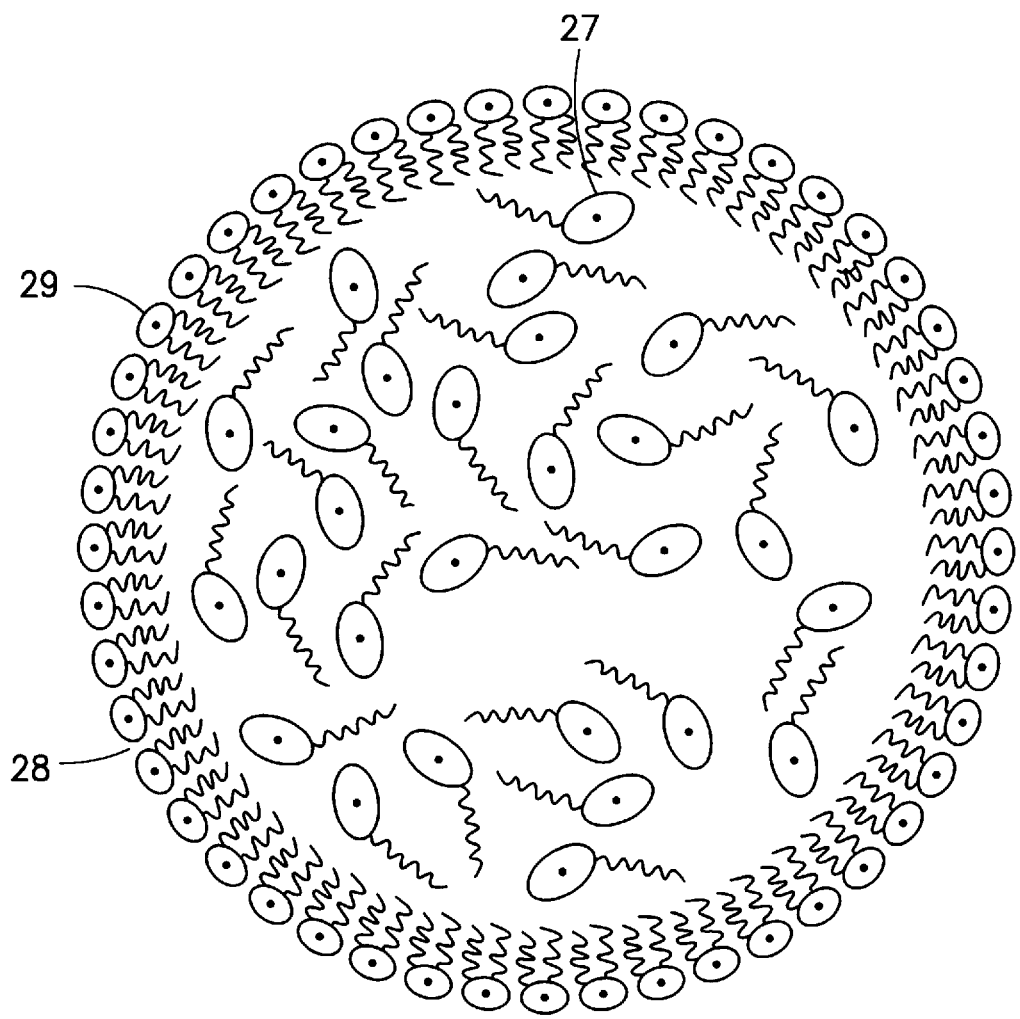
FIG. 2 is a variant of the donor particle of FIG. 1.

FIG. 2 shows the particle 29 produced by another method of preparation of the fluorescent neutral lipid donor. The emulsifier (PC) is replaced by phosphatide ("PL") 28 extract. The phosphatide extract is derived from egg, and includes phospholipid associated with the source. For example, lecithin >60%, phosphatyidyl-ethanolamine >15%, and lysolecithin <4%. The extract stabilizes the emulsion by providing charged emulsifying phospholipid. The charged phospholipid emulsify the fluorescent core comprised of NBD-CE 27 or other neutral lipid, producing a net charge associated with each particle. The net charge associated with each particle causes repulsion between the fluorescent donor particles thereby preventing fusion of the particles over time. The apolipoprotein apoA-I is eliminated by use of the PL extract. The emulsification process (sonication or microfluidization) is preferably performed at about 62 degrees centigrade (C) to 68 degrees C for about thirty minutes. Other temperatures, ranges and time periods can also be used.

Table 1 illustrates the raw data of transfer activity per microliter of human serum from a patient with high CETP activity. Table 2 illustrates the picomoles of labeled -CE transferred in 3 hours per microliter of serum or DTI transfer value units. Table 3 is representative of the DMSO dispersion of NBD fluorescent label versus fluorescent units.

The methods and apparatus herein are further used in mass screening projects to screen for compounds and isolation compounds that inhibit neutral lipid transfer protein at the different levels described above. The screening projects have a number of problems associated therewith that include the attenuation of fluorescent emission spectra of a fluorescent label used in an assay with a candidate inhibitor compound thereto. The attenuation is a result of the physical property of the candidate inhibitor compound, rather than the candidate inhibitor compounds effect on the lipid transfer protein at issue. By way of example, a dark green extract of a plant is added to the CETP or MTP assay system in a screening and isolation project. The assay system utilizes fluorescent techniques to determine is the extract is an inhibitor of the neutral lipid transfer protein, e.g. CETP or MTP. The dark green color of the extract interferes with the emission spectra detected by a fluorescence detecting device. The methods described herein allow for a calculable emission spectrum interference factor to be derived from the assay system by utilizing an additional fluorescent label or by broadening the bandwidth of the same label or by analysis of the emission spectra of a single label used. In addition, in mass screening and isolation projects, the method of MTP source is described in one variation as follows:

HepG2 cells are grown in 75 $cm^2$ T-flasks until confluent. The cells from about 6 flasks are suspended in a total of about 5 ml of homogenization buffer that may comprise 50 mM Tris-HCL, pH 7.4, 0.25M sucrose, 1 mM EDTA, 2 mM E600, 50 μg/ml $α_2$-Macroglobulin (with protease inhibitor activity), 0.01% $NaN_3$, (approximate protein concentration will be 10 mg/ml). The suspension is sonicated on ice with five 5 second bursts in a 550 W sonicator fitted with a microtip on power setting 4.50 μg of homogenate protein is used in the assay.

Alternately the homogenization buffer is made without E600 and $α_2$-Macroglobulin. Instead the homogenization buffer and the assay incubation buffer is made as follows:
1. Prepare 100 mM stock solution of Phenylmethylsulfonyl fluoride (PMSF Sigma P-7626) in ethanol.
2. Prepare 1mg/ml stock leupeptin (Sigma L-3402) in assay buffer (10 mM tris/150 mM NaCl/1 mM EDTA) pH 7.4
3. Add 500 μl PMSF stock and 2 ml leupeptin stock to 100 ml assay buffer use this as homogenization buffer and assay buffer.

The addition of protease inhibitors in the assay buffer serves a dual fold purpose of protecting the MTP from protease activity originating from the MTP source and protease activity originating from the test compound source.

By way of further example, an additional fluorescent label is incorporated into the assay system that includes an inert label that will not act as a measurement of lipid transfer protein activity nor interact with the lipid transfer proteins, e.g. neutral lipid transfer proteins. The additional label is present in the same system setup to measure activity, but the label is inert with respect to the lipid transfer proteins.

In another variant, the additional fluorescent label is bound to a substrate that interacts with of the lipid transfer protein (the label's emission spectrum may also be affected by the lipid transfer protein's activity) but the label is bound to the lipid transfer protein's substrate in a nonreactive (different) area. That is, the lipid transfer protein assay includes identical lipid transfer protein substrates with identical labels attached to the substrates, yet the labels with be located on different molecular areas of the substrates. The substrate of the lipid transfer protein is a lipid molecule that interacts with the lipid transfer protein. The location of the labels is specified so the emission spectrum of each entity is slightly shifted with respect to the other, thereby broadening the emission spectra or broadening the emission bandwidth.

The non-lipid transfer protein dependent labels, e.g. inert label, can be disposed on an inert substrate, independent of a substrate in the assay solution, as a portion of the acceptor particle, in the assay solution, as a portion of a fluorescent bead, or a component of the assay container or assay plate. The reference label, e.g. inert label, is utilized either in the assay solution or outside the assay solution. That electromagnetic radiation emitted by the reference label passes through the assay system and is read by a fluorimeter.

Figure 11A:
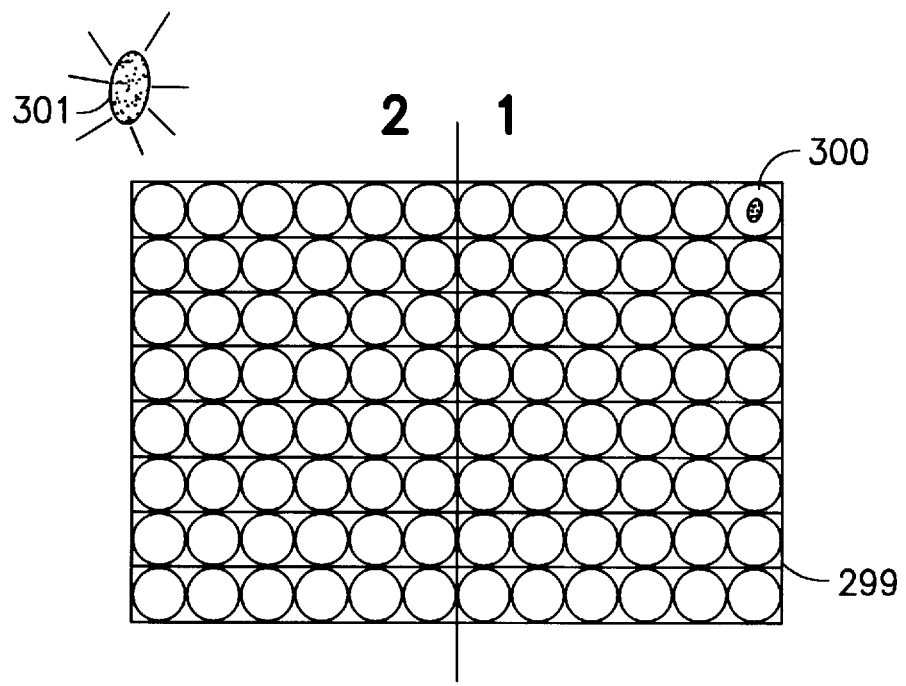
FIG. 11A is a diagram of microplate format of the invention.

FIG. 11A1 illustrates a microplate commonly utilized in assay of biological samples much like the auto-analyzers for blood in which the microplate handles a large number of samples. The invention provides a reference label which may be included in the plate construction so that the emission of the inert label passes through the lipid transfer protein assay. Plate 299 is comprised of many wells in which each may contain an assay for lipid transfer protein. The inert or reference label is molded into or "dropped" into the wells as depicted by well 300. Alternatively, as illustrated in FIG. 11A2 the inert label 301 is presented to the assay so the light of emission passes through the assay from beneath the plate.

Figure 11B:
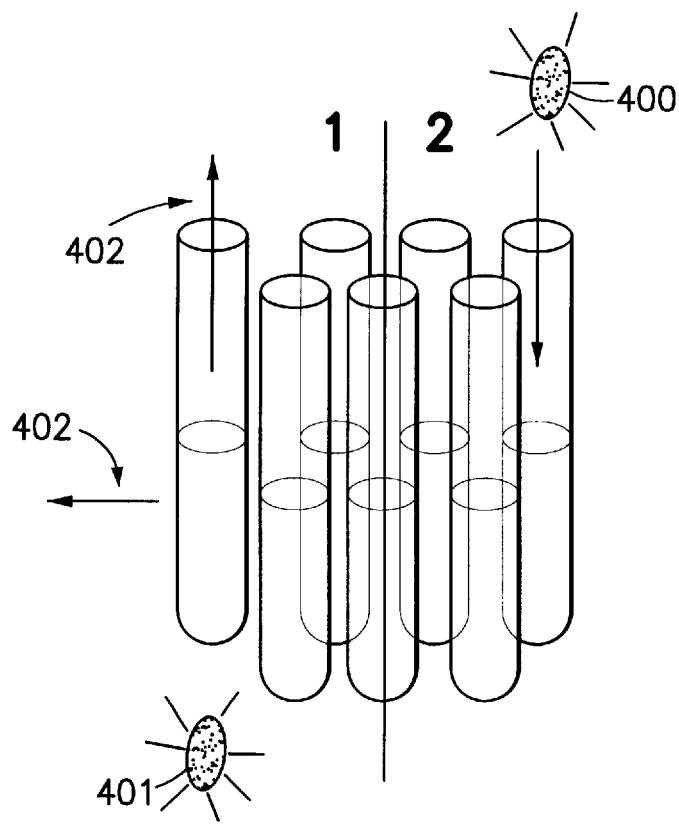
FIG. 11B is a diagram of a test tube format of the invention.

FIG. 11B1 is a diagram of the technique analogous to the technique utilized in FIG. 11A1,2; however when tubes are utilized in the assay system such as in an auto-analyzer for blood samples, the inert label may be added to the tube 400. Alternatively the inert label 401 is electromagnetically interacted with the lipid transfer protein assay by allowing the emission spectra of the inert label to be passed through the tube 402.

If the label for lipid transfer protein activity shares the excitation wavelength of the label used to determine spectral interference, the emission wavelength of the interference label is purposely shifted to distinguish between the peaks of the labels, or in the case of bandwidth broadening, the two peaks become one wide peak. The interference label is shifted to longer wavelengths than the emission peak of the activity measuring label because the longer wavelengths are more effected by spectral interference.

The methods described herein provide a screen that locates or screens out inhibitors of CETP, MTP, other lipid transfer proteins involved in the processes neutral lipid transfer protein conduct and the like. Broadly, the methods described herein are applicable in fluorescent measuring devices and methods where spectral interference is encountered. Where the fluorescent method or device has a label to follow lipid transfer protein activity, an additional label to follow the status of fluorescence efficiency is added. This is also true where one label is used in the assay but the bandwidth is broadened and the analysis of the data is used as a means to quantify spectral interference regardless of the type of fluorescence assay, lipid transfer protein or label.

The following examples discuss implementation of the invention at four levels: the donor particle level, the acceptor particle level, the molecular level and the instrument level. "Donor" particle refers to the particle responsible for donating cholesteryl ester or other lipid to a lipid transfer protein, e.g. neutral lipid transfer protein, and "acceptor" particle refers to the particle in the activity measurement system (assay) responsible for accepting cholesteryl ester or other lipid from the lipid transfer protein, e.g. neutral lipid transfer protein.

Figure 3:
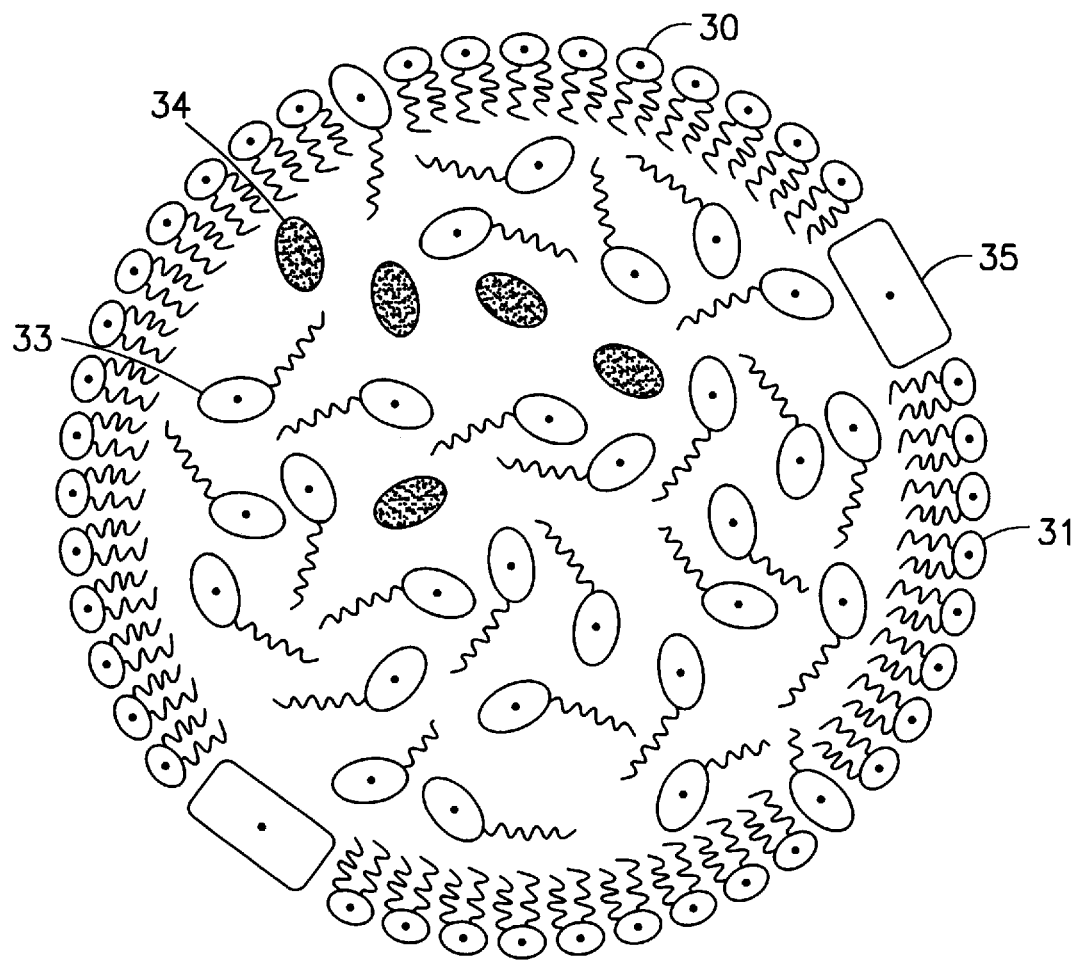
FIG. 3 is a variant of the donor particle of FIG. 1.

FIG. 3 illustrates a synthetic or synthesized particle 30 that includes an exemplary emulsion. The NBD-labeled neutral lipid NBD-CE 33 contained within the core of the synthetic particle will not yield a substantial fluorescent emission intensity when illuminated with excitation wavelength. Instead, the energy of the excited state is dissipated in radiationless energy transitions upon collision with other NBD-CE molecules. The non-fluorescent loss of energy is dependent upon molecular interactions associated with the core sequestered NBD-neutral lipid.

Figure 4:
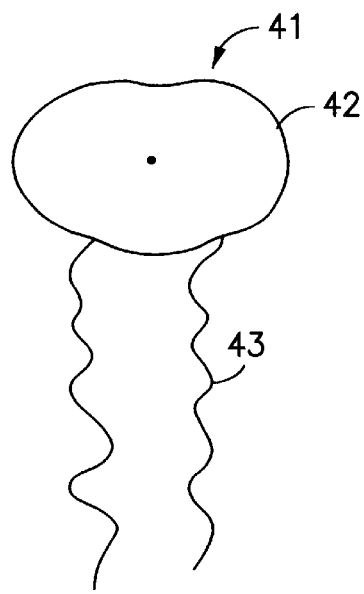
FIG. 4 is an emulsifier utilized in the kits apparatus and methods described herein.

The monolayer of PC molecules 31 of FIG. 1, in the synthetic particle 30, is further illustrated in FIG. 4. PC 41 is comprised of a polar head group 42, and non-polar or hydrophobic tail 43. The conditions under which the emulsification process is performed enables the non-polar or hydrophobic tail 43 of the PC molecule to partition with the hydrophobic NBD-neutral lipid, NBD-CE 33 of FIG. 3. The partitioning of hydrophobic constituents of the co-sonication mixture traps the NBD-neutral lipid or other self-quenching fluorescently labeled lipid into a small area relative to the area of the aqueous phase. The PC emulsified NBD-neutral lipid components are in stable non-aqueous or hydrophobic environment at high concentration with respect to collisional proximity and accordingly yield little fluorescence intensity.

Several approaches to measure spectral interference so the effect on the lipid transfer protein substrate fluorescence may be determined to ultimately give lipid transfer protein activity:

APPROACH I

At the level of the donor particle, an inert label is added when the particle is synthesized. The inert label is incorporated into the donor particle core by one of the following methods:

METHOD 1

A self-quenching fluorescent neutral lipid, such as exemplary NBD-CE 13, of FIG. 1 is emulsified by a suitable emulsifier such as a phospholipid, including by way of example, phosphatidylcholine ("PC") 41 of FIG. 4. Although the term emulsify is used, it is understood that numerous methods can be used to incorporate the NBD labeled lipid into a stable emulsified particle efficiently so as to achieve self-quenching emission characteristics of the label. Among techniques of emulsification, sonication and microfluidization (Microfluidics Corporation, Inc., Newton, Mass.) are two which provide a homogeneous particle size. The emulsion also optionally incorporates an inert label that is represented in FIG. 3. The stable emulsion illustrated in FIG. 3, is prepared by sonicating about 13 micromoles of N-(7-nitrobenz-2-oxal, 3-diazol-4-yl amino ("NBD") labeled lipid (CE or TG or other suitable lipid) 33, with about 13 mg of phospholipid ("PL") 31, and about 1.0 micromole of anthracenetrinitrobenzene ("ATNB") 34, at a power output in a 550 Watt sonicator of about 40 to 50%. A temperature above the melting point of the mixture of component lipids is maintained for about 45 minutes in a buffer of about 10 ml, of about 0.1M Kcl/about 10 mM trizma-HCL, pH of about 8. The sonicated mixture is rapidly cooled to a temperature of about 40 degrees centigrade. Then an apolipoprotein, such as 10 mg of apoA-I, 35 in about 2.5 molar urea is added in about less than 1 ml over about 15 min. at a sonication power of about half of that used for the high temperature sonication.

Where a particle similar to HDL is required, the resulting emulsion is ultra-centrifuged at a density of about 1.063 g/ml with a high density underlay of about 1.21 g/ml and a low density overlay such as about 1.006 g/ml overlay. The HDL density class particle is harvested form the 1.063 g/ml middle zone. The particle utilizes apolipoprotein apoA-I 35 for stabilization, similar to physiological conditions. Stabilization of the fluorescent donor is also accomplished with synthetic, amino acid peptides or a suitable protein such as casein.

METHOD 2

Figure 5:
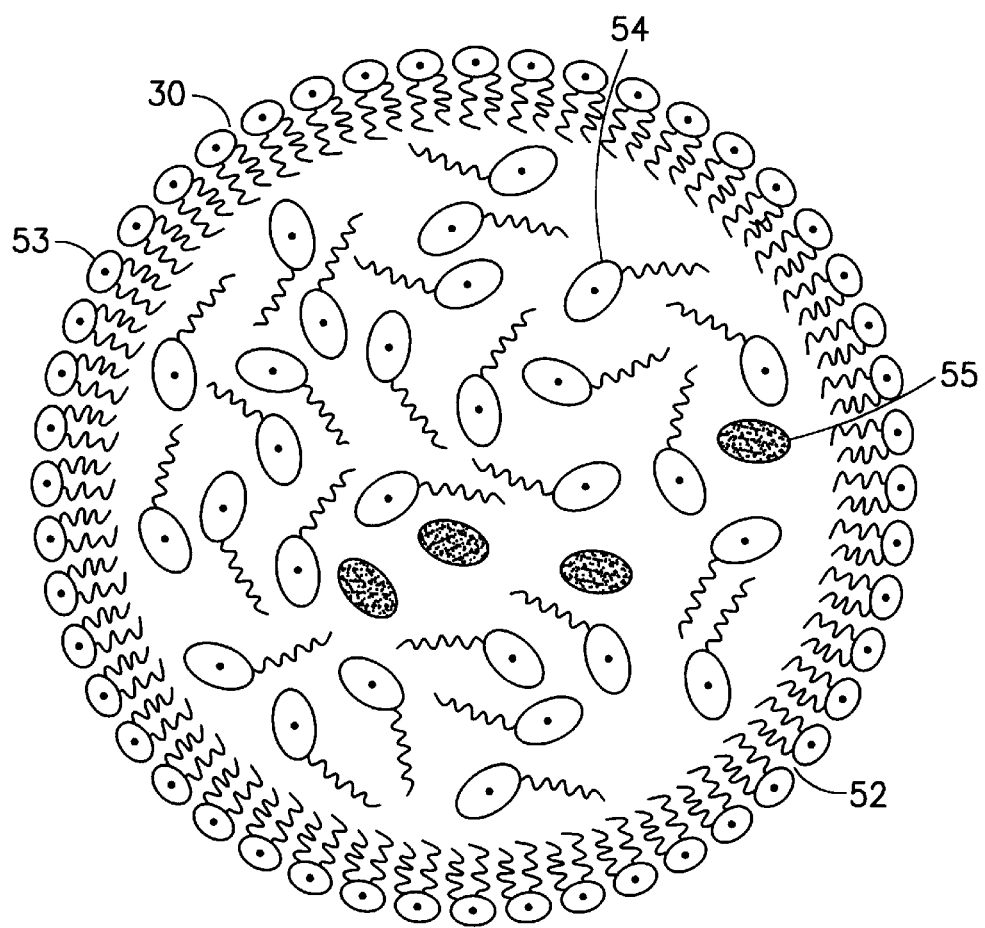
FIG. 5 is another variant of the donor particle of FIG. 1.

FIG. 5 shows the particle 52 produced by another method of preparation of the fluorescent lipid donor. The emulsifier (PC) is replaced by phosphatide ("PL") 53 extract. The phosphatide extract is derived from egg, and includes phospholipid associated with the source. For example, lecithin >60%, phosphatidylethanolamine >15%, and lysolecithin <4%. The extract stabilizes the emulsion by providing charged emulsifying phospholipid 53. The charged phospholipid emulsify the fluorescent core comprised of NBD-CE 54 or other lipid, e.g. neutral lipid, and ATNB 55, or label of emission maximum with a wavelength longer than NBD lipid, producing a net charge associated with each particle. The net charge associated with each particle causes repulsion between the fluorescent donor particles thereby preventing fusion of the particles over time. The apolipoprotein apoA-I is eliminated by use of the PL extract. The emulsification process (sonication or microfluidization) is performed at about 62 degrees centigrade (C) to 68 degrees C. for about thirty minutes.

METHOD 3

Lipid transfer protein substrates with labels that are labeled in different molecular locations or the substrates having different labels are used in the third method described herein. The fluorescent emission spectrum of a fluorescent label varies according to the molecular environment of the label. IF the NBD label of NBD-CE is covalently bound to the CE in different areas a broader emission band width will result.

METHOD 4

The fourth method of incorporating the interference label into the core of the donor particle includes injection of about 1.0 micromole of ATNB dissolved in about 5 microliters of dimethylsulfoxide ("DMSO") into about 2 ml of prepared donor emulsion (referred to herein as "the DMSO partition method of labeling").

APPROACH II

Approach II utilizes the acceptor particle as the carrier of the inert label. A triglyceride emulsion is prepared from 1.0 gm of soybean oil, 0.124 gm of PL, 0.225 gm of glyceride and 1.0 micromole ATNB in 10 ml of distilled water by sonication. ATNNB is DSMO partitioned into the core of a TG emulsion. Alternatively, the acceptor for the NBD-neutral lipid is human LDL or VLDL and if spectral interference occurs the standard may be DMSO partitioned into these lipoproteins.

APPROACH III

In the third approach, a separate particle of solely emulsified, inert label (premixed with the fluorescent cholesteryl ester donor and acceptor of the inert particle) is added separately to the assay mixture.

APPROACH IV

The fourth approach presents the inert label to the lipid transfer protein assay mixture bound to a solid bead or matrix. The inert label has certain spectral characteristics according to the spectral characteristics of the labeled cholesteryl ester or the substrate of the lipid transfer protein under test. In order to accurately determine the spectral interference, the inert label should have an emission maximum of equal or longer wavelength than that of the non-inert, labeled substrate. An inert label with emission maximum at equal or longer wavelengths than the labeled substrate ensures an accurate measurement of spectral interference caused by the colored or otherwise interfering compound. The interference or attenuation of emission energy will be more pronounced at longer wavelengths because the photons are less energetic than photons of shorter wavelength. This will provide a means to quantify the influence of a colored compound on the fluorescent label involved with lipid transfer protein activity. The inert label optionally has the same or different excitation wavelength. If the inert label has an excitation wavelength that is the same as the lipid transfer protein substrate or non-inert label, the emission maximum of the inert label must be shifted toward longer wavelengths. If the excitation wavelength of the inert label is different than that of the substrate or non-inert label the emission maximum of the inert label may be equal to the non-inert label.

Figure 6:
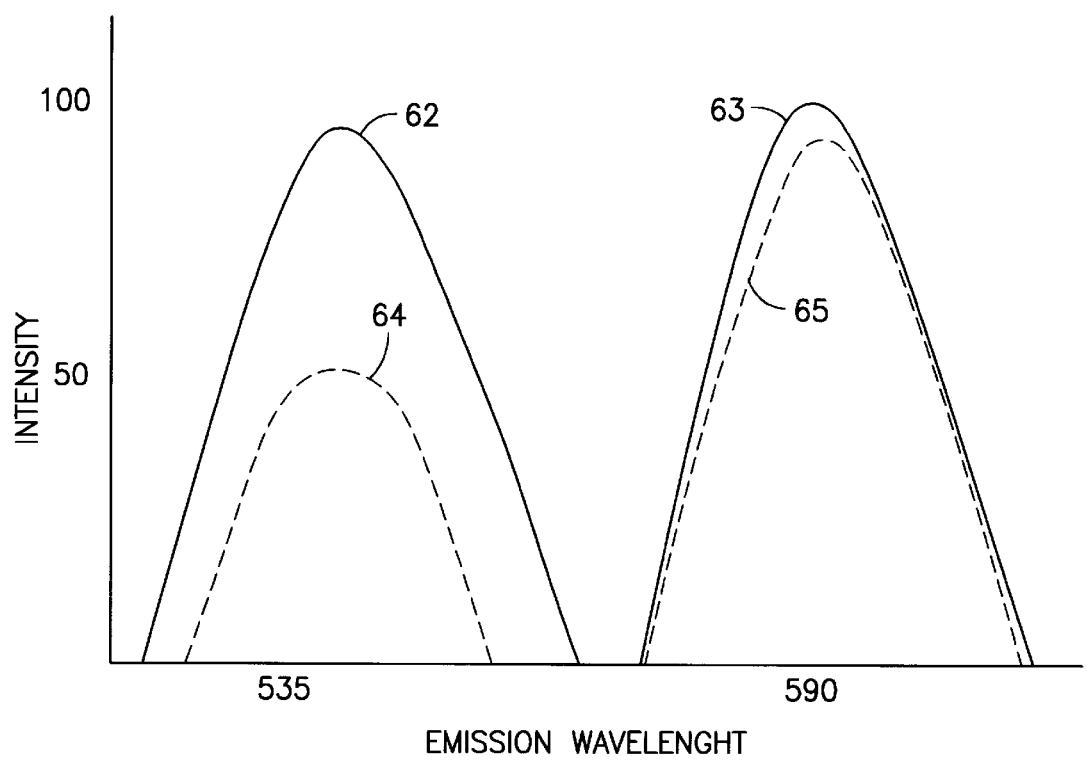
FIG. 6 is a graph of the intensity vs. wavelength for an exemplary donor particle.

As illustrated in FIG. 6, the NBD-fluorescent label covalently bound to cholesteryl ester of NBD-CE, incorporated into the core of an emulsion particle with ATNB, excited at 465 nm, yields an emission spectra as depicted. The distribution of fluorescent intensity form 500 nm to 600 nm (x-axis) reveals the emission fluorescence intensity (Y-axis) maximum at 535 nm at 62, for the NBD-CE and the emission maximum of the ATNB at 590 nm at 63. The plots of emission intensity 62, 63 represents the results obtained from a control that demonstrates transfer and no disturbance of emission intensity. Dotted line 64 and dotted line 65 represent a control without transfer protein added and, accordingly low emission intensity at the 535 nm wavelength. The ATNB emission intensity is unchanged, indicating no spectral interference.

Figure 7:
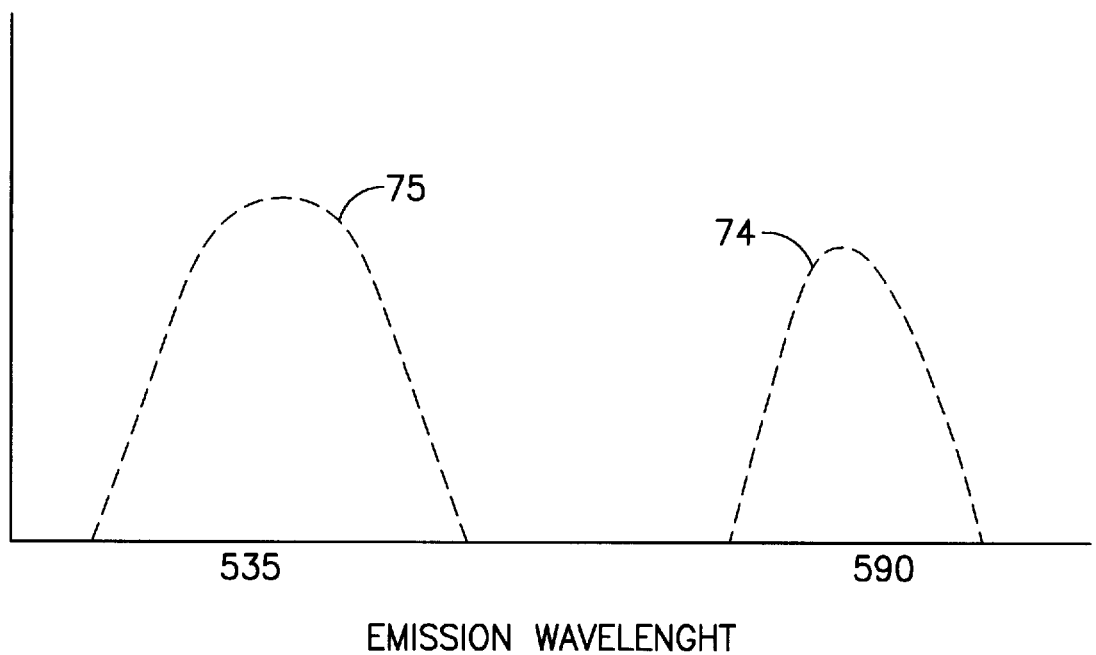
FIG. 7 is a graph of the intensity vs. wavelength for an exemplary donor particle wherein there is spectral interference.

FIG. 7 illustrates the result of an interfering or colored compound on the NBD and ATNB emission spectra. The ATNB peak at 74 is approximately 40% of the control and the NBD peak at 75 is approximately 50% of the control. This result, without the presence of the ATNB peak, would be falsely interpreted as the IC50 or concentration of inhibitor at 50% inhibition of the lipid transfer protein. The emission spectra of the ATNB changes only when the assay is confronted with a colored or otherwise interfering compound, and it is affected to a greater degree than the shorter, more energetic light emitted by the NBD. The NBD label, however, is affected by both transfer protein activity and spectral interference. Applying this concept to an interference detecting label with a different excitation wavelength than the label used to measure transfer protein activity, requires the spectra be collected under each excitation to determine the status of each label. Many other combinations of fluorescent label pairs are sufficient for measurement of spectral interference even those with emission maximums below the label for transfer measurement.

Figure 8A:
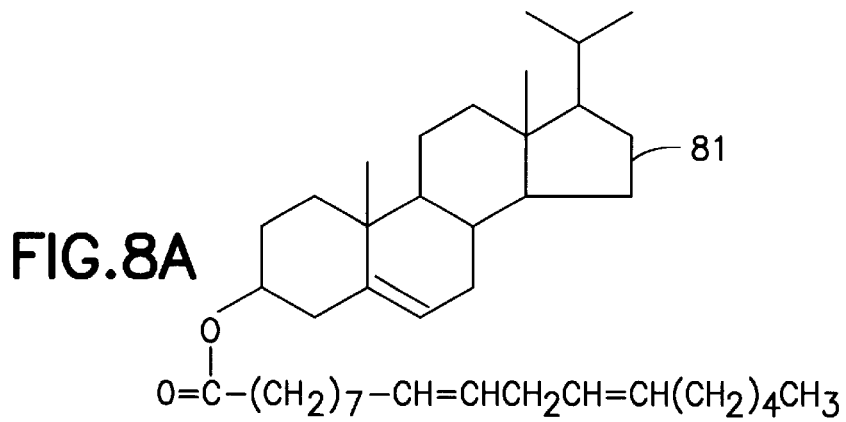
FIG. 8A is a diagram of a cholestryl ester.
Figure 8B:
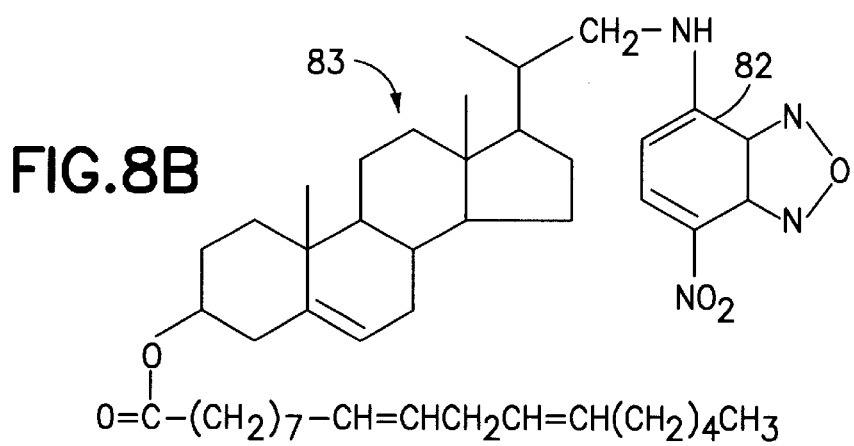
FIG. 8B is a diagram of fluorescently labeled lipid of FIG. 8.
Figure 8C:
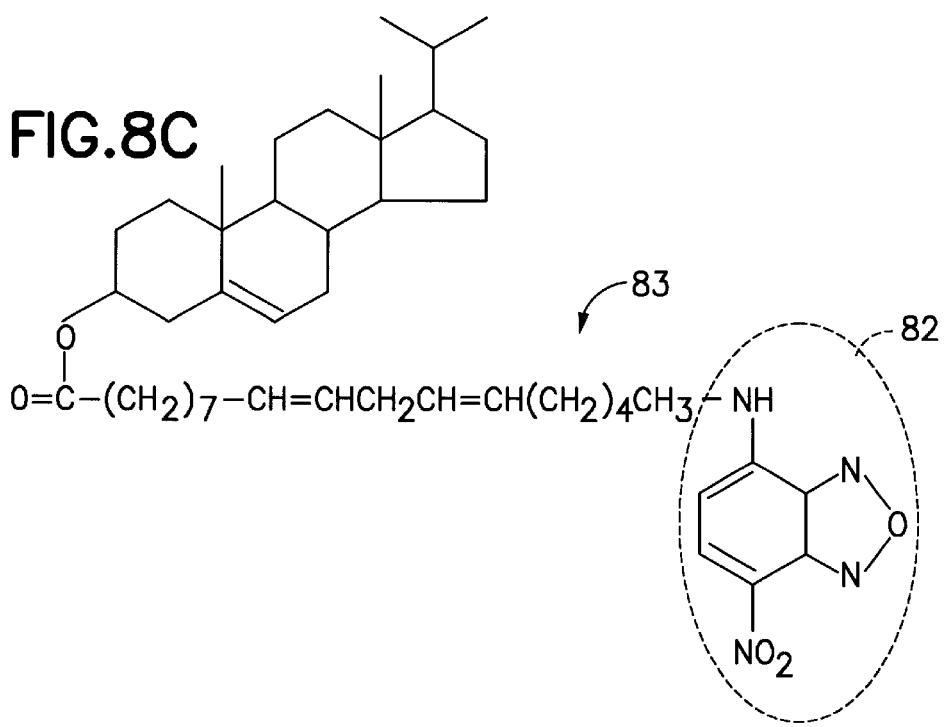
FIG. 8C is a diagram of fluorescently labeled variant of FIG. 8A.

In yet another variant, one label is bound to the same species of substrate in different areas on the substrate molecule. As illustrated in FIG. 8A, cholesteryl ester (CE) 81 has the NBD 82 fluorescent label bound to different areas of the CE molecule in the formation of the fluorescent labeled NBD-CE as illustrated in FIG. 8B. The emission spectra of a mixture of these two substrates will be broader than the one studied separately, or one will be of slightly longer wavelengths than the other.

Figure 9:
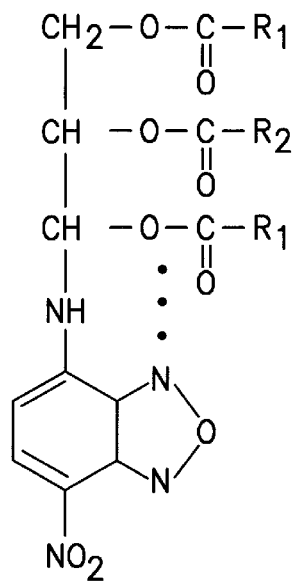
FIG. 9 is a diagram of a fluorescently labeled substitute of a lipid transfer proteins.

In yet another variant of broadening the emission spectra, a different substrate of the lipid transfer protein is included in the assay. For example, NBD labeled TG is illustrated in FIG. 9 in a neutral lipid transfer protein assay. A mixture of NBD-TG and NBD-CE included in the assay also broadens the emission spectra of the assay.

The efficiency of the fluorescence is determined from the loss of peak broadness as the lower energy (longer wavelength) emission is affected relative to a control. In other words, if an lipid transfer protein inhibitor is present in the assay, the bandwidth will be proportional to a control, but the intensity will be less than the control. If a compound is interfering with emission efficiency the band width is disproportionately narrower than the control. Bandwidth broadening by specifying attachment of the label to alternate molecular environments in the excited state, providing alternate pathways to the ground state, causing spectral shifts in identical substrates.

In utilization of the method and apparatus to discover inhibitors of lipid transfer proteins, the method is practiced as described herein except that a compound of plant or fungal or other origin is added in the assay system with the lipid transfer protein so that if the compound is an inhibitor of the protein, the assay will indicate no transfer activity—as if the protein where absent. The compound is then further purified. For example, if a fractionation method, such as a silica column, of compound purification is utilized, the respective fractions would each be assayed for inhibitory effects upon the lipid transfer protein. The fraction(s) with inhibitory activity would be pooled and further purification methods would be used to render the mixture down to a pure compound. Each step of purification would include an assay step to determine the purification status of the inhibitory compound. Upon purification of the compound, derivatives of the purified compound are made and each derivative is assayed according to the invention to determine if the derivative or addition of functional groups increases the inhibition activity of pure compound. In addition, determination of the chemical structure of the inhibitory compound allows similarity searches for compounds of similar structure to be tested as a transfer protein inhibitor according to the invention.

A method and apparatus for rapid and accurate determination of neutral lipid transfer protein activity utilizing fluorescence, in a sample that would otherwise yield inaccurate results due to spectrally interfering components is provided herein. The method and apparatus allow users in the field to determine the relative activity of neutral lipid transfer protein in the presence of inhibitors of the lipid transfer proteins and without the utilization of radioisotopes. Further, the method and apparatus provide the benefit of obtaining readings in shortened periods of time over other methods and devices, and allow for sample volumes that are many fold less than those required by other assay systems.

Generally, the methods and kits disclosed herein have the benefit of not requiring separation of donor and acceptor particles. Likewise the constituents assayed herein do not have to be reisolated to obtain lipid transfer protein activity values.

The method and the apparatus indicate to a physician, or other user, if a patient has high CETP activity, low CETP activity, or otherwise abnormal CETP activity so that the physician, or other user, may recommend modification of the patient's diet, or other treatment, before atherosclerosis is evidenced, or before there is an elevation of a risk factor for the condition.

A non-radioactive kit that includes a labeled lipid derivative that emits electromagnetic radiation upon excitation is provided herein that is readily usable for the purpose of performing simple, rapid and accurate tests to determine activity of CETP in a patient or group of patients. The lipid derivatives and included derivatives of lipids with self-quenching labels such as, NBD, Bodipy™ commercially available from Molecular Probes, Inc. of Eugene, Oreg. or concentration dependent florescent labels such as pyrene. The kit further does not require the separation of donor or acceptor particles to accomplish activity measurements, thereby decreasing labor and resource costs and yields a real time activity. Further, the reagent substrate emission is not subject to quenching by oxygen.

A physician, or other user, is provided a kit, diagnostic device, and method for indicating if a child or adult has high CETP, or otherwise abnormal CETP activity so that the physician can recommend treatment, e.g. modification of the individual's diet before atherosclerosis is evidenced, a CETP inhibitor, or other CETP treatment.

The diagnostic kit or device for CETP activity or other lipid transfer protein measurement includes a suitable, e.g. an effective amount, of synthetic NBD-labeled neutral lipid emulsion and buffer to a first container. Exemplary amounts include an effective amount of synthetic NBD lipid or other fluorescently labeled lipid transfer protein in an emulsion, in the range of 100 picomoles to 600 picomoles, and an effective amount of buffer, in the range of about 100 microliters to about 500 microliters, this yields a concentration range of about 500 pmoles to about 5000 pmoles of emulsified NBD lipid per milliliter of buffer, preferably 200 microliters of buffer. Twice this amount is still within the range of effectiveness for the assay but at some point greater than 5000 pmoles per ml of neutral lipid the assay donor will become the substrate of choice for lipid transfer protein to back transfer the to a self quenched state. The preferred buffer includes an effective amount, e.g. 10 millimoles (mM) of trizma hydrochloride (HCl), an effective amount, e.g. 150 mM of sodium chloride (NaCI) and an effective amount, e.g. 2 mM of ethylenediaminetetraacetic acid (EDTA), all buffered to an effective pH, e.g. about pH 7.4. An effective amount or suitable amount of acceptor particle or emulsion, such as VLDL or a synthetic phospholipid/TG emulsion is then added to the buffered mixture in the first container for the purpose of accepting the transfer of neutral lipid. The acceptor functions as the sink for CETP mediated labeled neutral lipid transfer from the donor source. An effective amount of CETP or other lipid transfer protein source is then added to the solution in the first container. Optionally, a control for measurement purposes is added to a second container made the same ways as the first container, except that the CETP or other lipid transfer protein source is not added to the second container, and instead a volume of saline solution, or the like, is added as a control. The volume of saline solution is equivalent to the volume of the CETP or other lipid transfer protein source in the first container. In a variant, both containers contain plasma or other CETP or other lipid transfer protein source, and one container is established as a control by incubation at an effective temperature, e.g. about 4 degrees centigrade.

There are various lipid emulsions or lipoproteins that may be used herein as an acceptor; VLDL is a preferred acceptor.

Both containers are incubated at an effective temperature, e.g. about 37 degrees centigrade, for a suitable time and the fluorescence at about 538 nanometers (nm) is read at an excitation wavelength of about 465 nm in a standard laboratory fluorimeter. The first container, that received the human plasma or other CETP or other lipid transfer protein source, is observed in the fluorimeter as increasing in fluorescence intensity over the incubation period. The second container, not receiving plasma or other CETP source but receiving a volume of saline solution, would not change in fluorescence intensity when measured in the fluorimeter. The background florescence is determined by the second container and the intensity value subtracted from that of the first container. The kit and method is independent of the proportions present of the prepared sonicated particle, the acceptor emulsion and the CETP or other lipid transfer protein source. The kit and method requires the addition of the synthetic particle at an effective amount within the detection limit of the fluorimeter used for the measurement. The ratio of the acceptor emulsion or particles to the synthetic particles is kept high enough so that intra-particle transfer of NBD-CE between synthetic donor particles does not occur. Additionally, the diagnostic kit is formulated with standard proportions to allow activity measurements of CETP or other lipid transfer protein to be compared from laboratory to laboratory.

Figure 10:
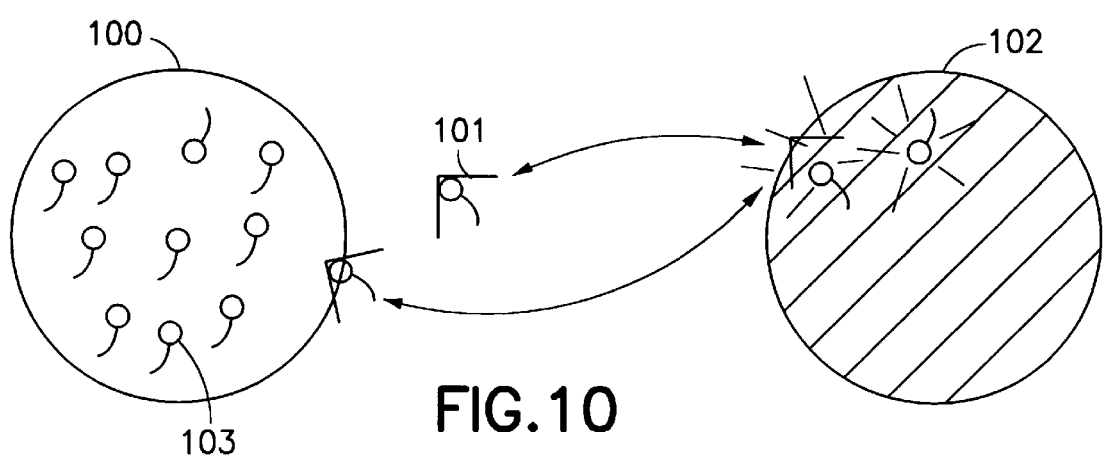
FIG. 10 is a schematic diagram of a transfer process described herein.

FIG. 10 illustrates a schematic of the lipid transfer protein transfer process measured by the kit or diagnostic device. Donor 100 retains NBD-neutral lipid self quenched within its core. Of course, other self-quenching fluorescent labels other than NBD are also contemplated herein. The lipid transfer protein 101, e.g. neutral lipid transfer protein, shuttles the lipid, e.g. neutral lipid, to acceptor 102 where it fluoresces in the unquenched state. The kit includes a vial with an effective amount, e.g. about 1 milliliter (ml) of a liquid mixture that comprises an effective amount, e.g. approximately about 50 to 120 nmoles of emulsified NBD-neutral lipid. The kit also includes a vial with an effective amount, e.g. about 1 ml of a solution comprising VLDL diluted to an effective amount, e.g. approximately about 1 milligram of protein with the preferred buffer to act as the acceptor. Optionally, approximately equal volumes of each vial or container are dispensed into a sample container. A volume of about 1/400 th to 1/100 th of the total volume of a patient's plasma or other CETP source is added, and the mixture is allowed to incubate with the change in fluorescence intensity monitored as described herein.

As shown in FIG. 10, the transfer process includes the CETP 101 or other lipid transfer protein interacting with the prepared synthetic NBD-CE emulsion 100 or other fluorescently labeled lipid and shuttling NBD-CE molecules 103 away form the core of the emulsion. The CETP 101 or other fluorescent label releases the NBD-CE 103 to an acceptor particle 102. The fluorescent intensity of the NBD-CE increases as the NBD-CE is moved from the synthetic HDL type sonicated emulsion 100 to the acceptor particle 102.

The diagnostic kit is a valuable tool. It is used to screen a large population of patients to uncover those with genetic idiosyncrasies related to lipid transfer protein such as hyperalphalipoproteinemia (a disorder characterized by the absence of CETP in humans), hypoalphalipoprotenemia, and the like. It is used to screen for antibodies to CETP or other lipid transfer protein in a large number of samples, and to identify other inhibitors of CETP or lipid transfer protein.

Figure 12:
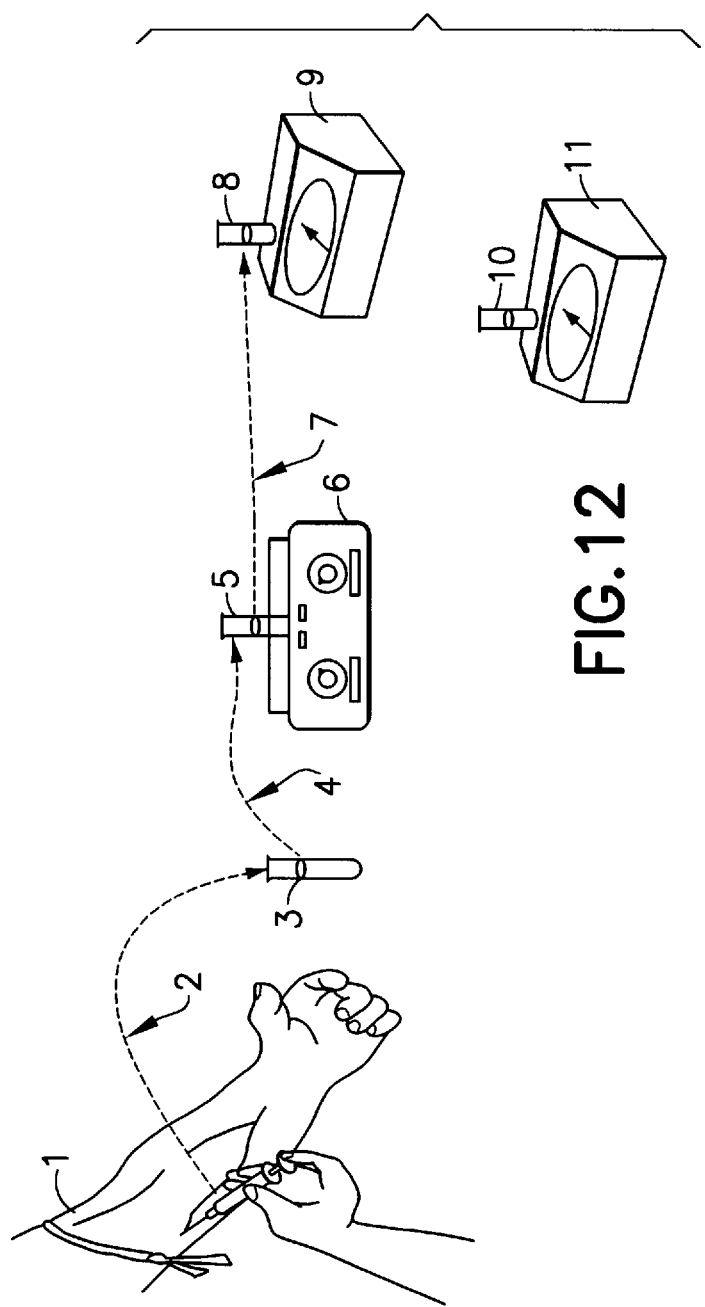
FIG. 12 is an illustration of the invention applied to a patient study.

FIG. 12 illustrates the method of the invention as a patient heart disease diagnostic device that measures the activity of lipid transfer protein, e.g. CETP, where a sample of blood is withdrawn from patient 1 and transferred 2 to the assay tube 3. Optionally, the transferal step 2 of whole blood to the assay tube 3 may include a step that includes centrifugation of the whole blood or some other means of separation of the plasma or other components of the whole blood. The sample is combined with the assay fluorescent lipid donor and acceptor in a buffered solution 3 and an optional baseline fluorescence value at zero time is read by fluorimeter 10 as indicated by tube 10. The incubated assay solution 5 with donor and acceptor is incubated in incubator 6, to obtain an incubated solution. The solution 3 is incubated at a suitable temperature which includes room temperature in incubator 6 for a suitable time period. The incubated mixture 8 is then transferred, as indicated by step 7, to fluorescent spectrometer 9 at which point the fluorescent intensity is determined.

Figure 13:
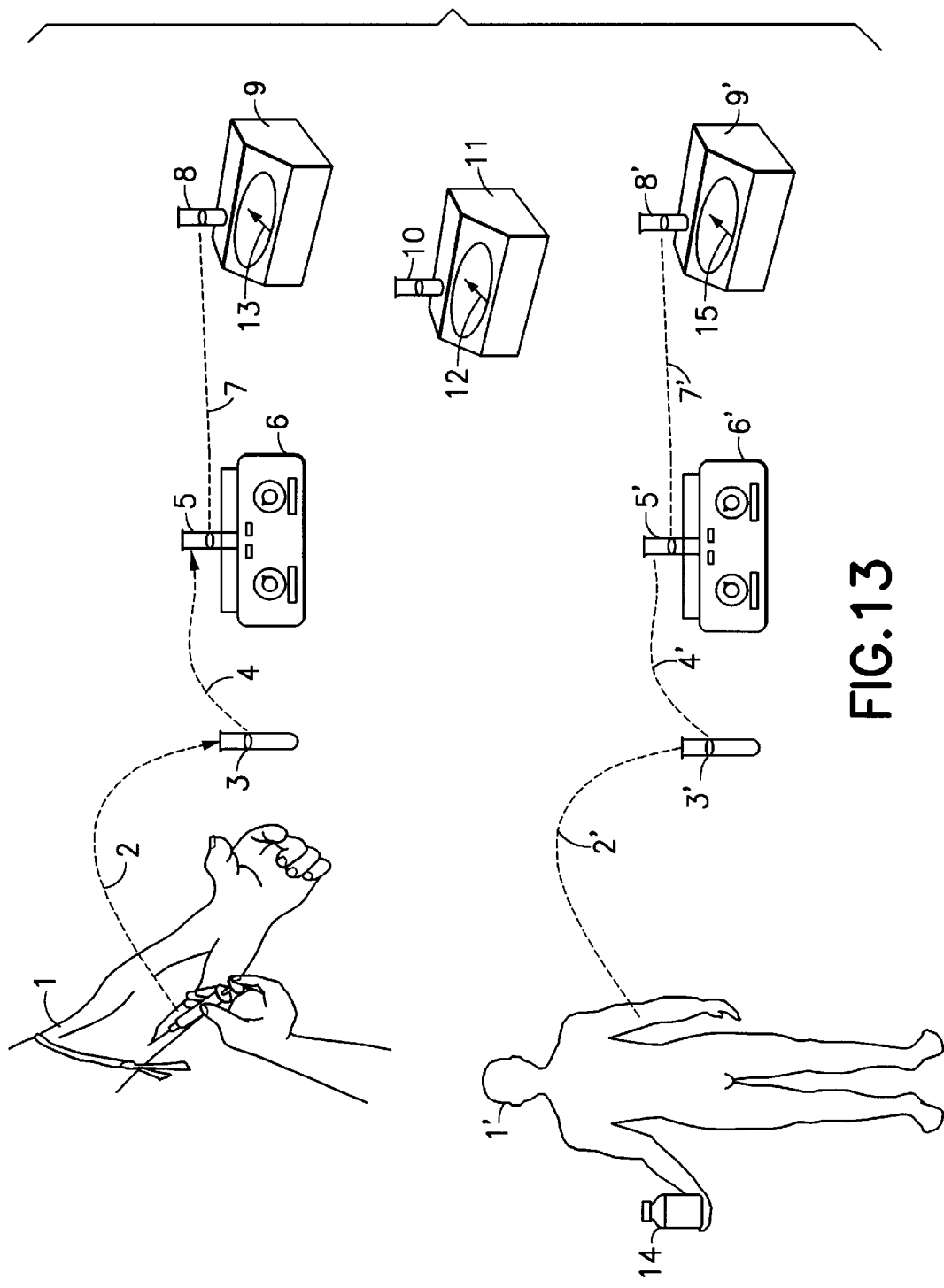
FIG. 13 is an illustration of the invention applied to applications that include testing the efficacy of a treatment program.

FIG. 13 illustrates the invention with respect to treatment of coronary heart disease and determining the efficacy of treatment methods for heart disease. The numbers of FIG. 13 correspond to the numbering of FIG. 12 except for the additional step that includes the treatment 14 being administered to the patient, that exhibits an abnormal lipid profile or abnormal lipid transfer activity. The patient's blood sample CETP transfer activity is then reassessed according to the invention as illustrated by the prime number steps of FIG. 13 similar to that of FIG. 12.

Figure 14:
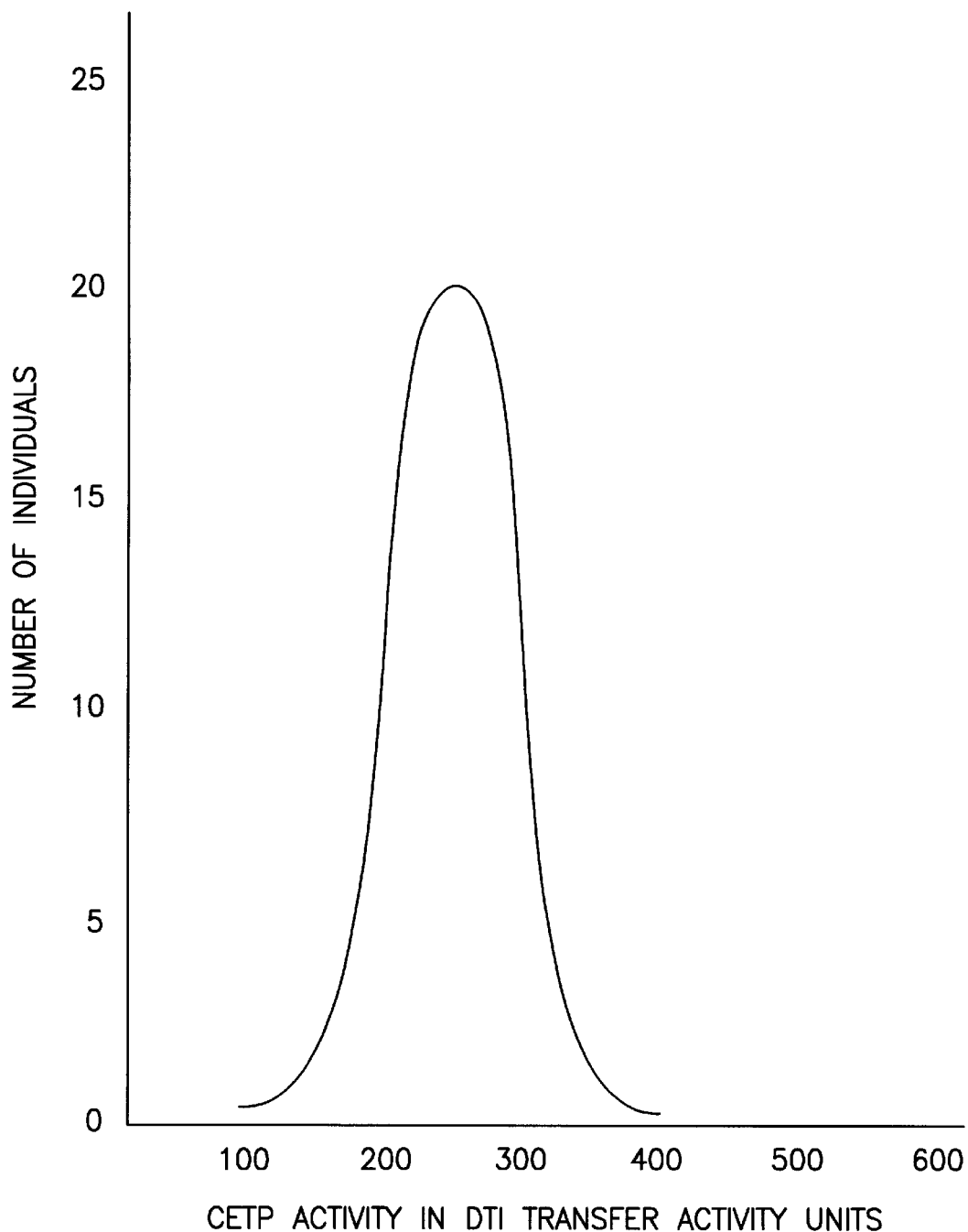
FIG. 14 illustrates a patient distribution of activity of CETP.

FIG. 14 illustrates utilization of the method and derives a gaussian distribution of patient data to derive standardization from groups of patients in order to determine those patients with abnormalities associated with lipid transfer protein, such as CETP. FIG. 14 illustrates a broad base of patients measured and transfer activity measurements relative to patients with normal lipid profiles or of normal risk to coronary heart disease. The normal range of DTI transfer activity units is expressed in FIG. 14. The curve of FIG. 14 is obtained by selecting normolipidemic subjects and measuring CETP or other lipid transfer protein activity. Statistical methods are known in the art for obtaining mean, median and other values associated with this type of distribution.

Figure 15:
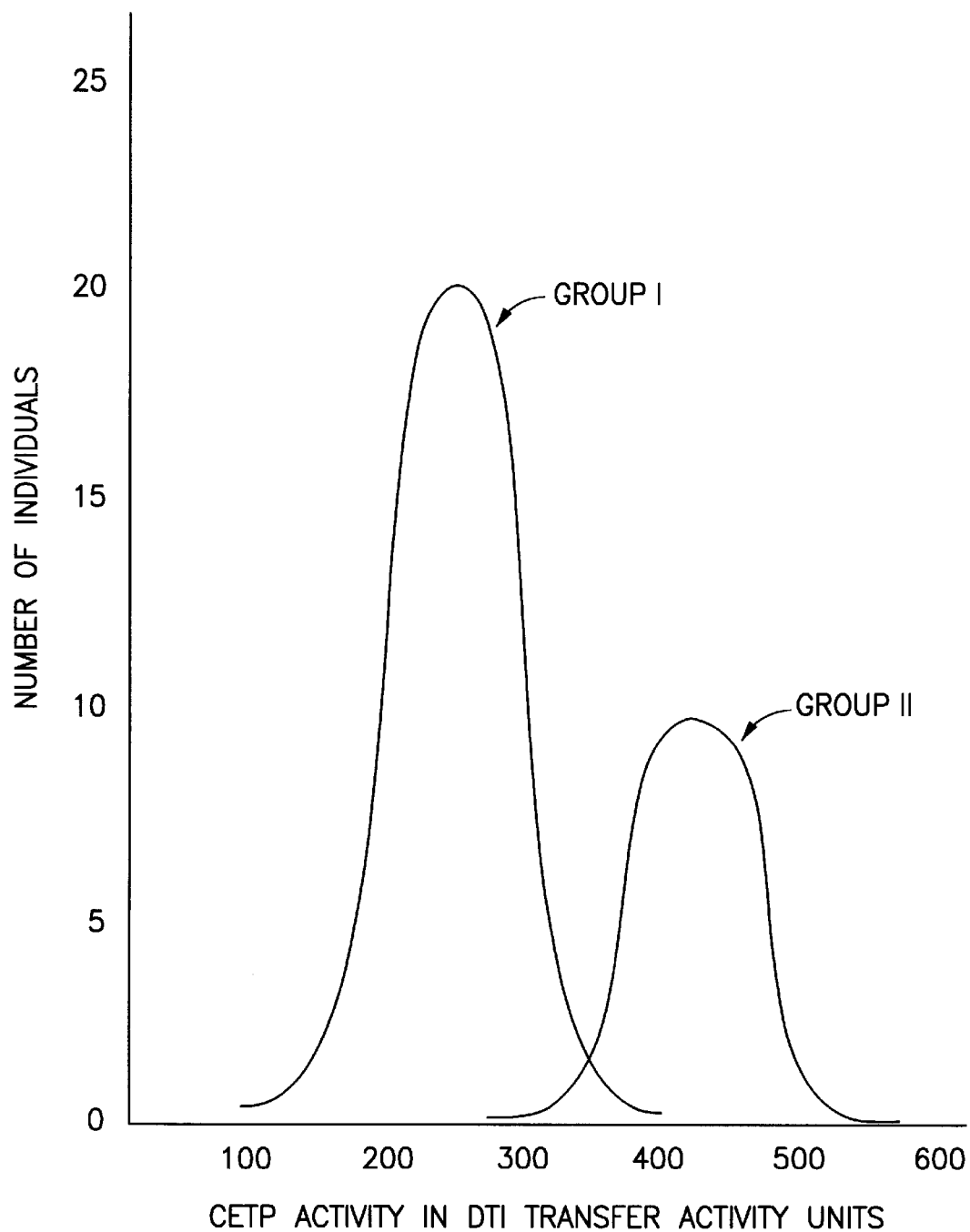
FIG. 15 illustrates a patient distribution of transfer activity.
Figure 16:
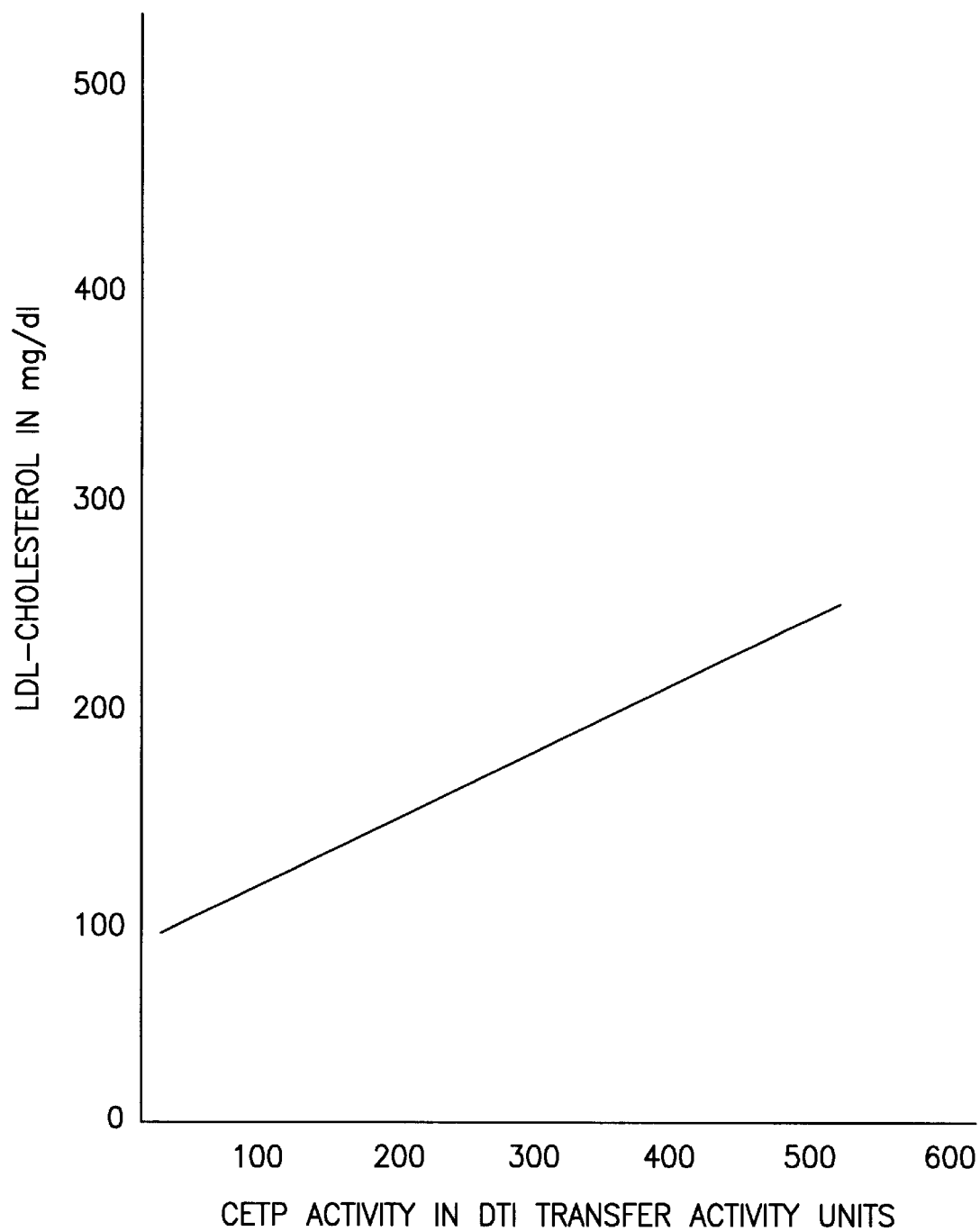
FIG. 16 illustrates a LDL cholesterol versus CETP activity graph.

FIG. 15 illustrates the DTI transfer activity of a group of patients with high CETP activity (GROUP II) superimposed on a graph of patients with normal CETP activity (GROUP I). The frequency versus CETP activity in a random group of patients is illustrated in FIG. 16. The graph of FIG. 16 indicates that LDL-cholesterol and CETP activity is found to increase in a subject group.

The method for measuring the activity of cholesteryl ester transfer protein or MTP comprises the steps of: adding a prepared emulsion particle to a buffer solution simulating physiological conditions, and adding an emulsion of lipid to the buffered solution of prepared sonicated particle. The lipid emulsion includes an acceptor particle to accept neutral lipid transfer protein mediated transfer of a fluorescent neutral lipid such as, NBD-CE or NBD-TG. The acceptor lipid emulsion is a commercially available VLDL. The method further comprises the step of adding a source of neutral lipid transfer protein to the buffered solution, and adding a compound to the buffered solution for the purpose of testing the compounds effect on the neutral lipid transfer protein, namely, neutral lipid transfer protein activity. The CETP source is human plasma in one variant. The MTP source is liver, intestinal cell homogenate or yeast cell extract in another variant. The method further comprises the step of incubating the buffered mixture, reading the fluorescence of the mixture, and calculating the effect of the compound on the emission spectra of the transfer label so transfer activity can be accurately determined.

In quantifying the transfer of fluorescent CE mass the method included in the invention may be utilized as follows:

The standard curve to derive the relationship between fluorescence intensity and mass transfer may be generated by dispersing donor particle in isopropanol. Spectrally pure (HPLC grade or better) isopropanol is utilized as the solvent, there should be no background fluorescence when isopropanol alone is read.

For example, prepare six test tubes labeled from 'T0' to 'T5' each containing an effective amount, e.g. 1 ml isopropanol, add an additional effective amount, e.g. about 1 ml of isopropanol to tube 5. Pipette an effective amount, e.g. about 5 μl donor particle to the test tube labeled T5, thoroughly mix (vortex) to adequately disperse the donor particle in the isopropanol. To check the solution for sufficient dispersion of the NBD-CE, a sample may be read in the fluorimeter (EX 465/EM 535). If the fluorescence intensity gradually increases, the sample is improperly mixed because the NBD-CE is still being dispersed (i.e. becoming "unquenched"). A constant fluorescence intensity reading of the sample indicates proper dispersion of the donor. Transfer an effective amount, e.g. about 1 ml T5 (conc.=X/2 μg NBD-CE/ml isopropanol) to the test tube labeled 'T4'. Mix and pipette an effective amount, e.g. 1 ml from tube '4' to tube '3', vortex tube '3'. Pipette an effective amount, e.g. 1 ml from tube '3' to tube '2', vortex tube '2'. Pipette an effective amount, e.g. 1 ml from tube '2' to tube '1', vortex. Read the fluorescence intensity (EX 465/EM 535) of the samples from tubes T0 to T5.

The fluorescence intensity values of the standard curve be may applied directly to your experiments.

| Prepare | Read 1 ml | Fl. Int./200 μl × 2 | |
|---|---|---|---|
| 5 μl donor in 2 ml isopropanol | T5 | 2350 | 2291 |
| 1 ml T5 + 1 ml isopropanol | T4 | 1189 | 1189 |
| 1 ml T4 + 1 ml isopropanol | T3 | 628 | 655 |
| 1 ml T3 + 1 ml isopropanol | T2 | 359 | 359 |
| 1 ml T2 + 1 ml isopropanol | T1 | 192 | 232 |
| 1 ml isopropanol | T0 | 38 | 53 |

While only a few preferred embodiments of the invention have been described herein above, those of ordinary skill in the art will recognize that the embodiment may be modified and altered without departing from the central spirit and scope of the invention. Thus, the preferred embodiment described herein above is to be considered in all respects as illustrative and not restrictive, the scope of the invention being indicated by the appended claims, rather than by the foregoing description, and all changes which come within the meaning and range of equivalency of the claims are intended to be embraced herein.

I claim:

1. A non-radioactive method of simplifying the determination of a coronary heart disease risk factor comprising the steps of:
   (a) obtaining a sample of plasma from a mammal having a source of lipid transfer protein;
   (b) incubating for an effective time period the sample in a non-radioactive lipid transfer protein assay to obtain an incubated sample;
   (c) measuring fluorescent emission of the lipid transfer protein activity of the incubated sample to determine a lipid transfer protein activity value; and,
   (d) comparing the sample's lipid transfer protein activity value to a predetermined standard value.

2. The method of claim 1 in which the non-radioactive lipid transfer protein assay is a Diagnescent™ kit.

3. The method of claim 1 in which incubating further comprises the steps of adding a prepared sonicated particle to a buffer to form a buffered solution, and adding an emulsion of lipid to the buffered solution to accept the transfer of a neutral lipid from the sample.

4. The method of claim 1 in which the lipid transfer protein is selected from the group consisting of CETP and MTP.

5. The method of claim 1 in which the source has a naturally occurring concentration of CETP and in which measurements are taken without need for isolation or purification of CETP from the sample.

6. The method of claim 1 in which the source comprises an effective amount of plasma and has a naturally occurring concentration of CETP.

7. The method of claim 1 in which the sample of plasma from which the reading of CETP activity is obtained in the range of about 1 microliters of plasma to about 3 microliters of plasma.

8. The method of claim 1 in which the sample is human blood.

9. A non-radioactive method of simplifying the screening for defects in the gene coding for lipid transfer protein that affects said protein's activity comprising the steps of:
   (a) obtaining a sample from a mammal having a source of lipid transfer protein;
   (b) incubating for an effective time period the sample in a non-radioactive lipid transfer protein assay to obtain an incubated sample;
   (c) measuring fluorescent emission of the lipid transfer protein activity of the incubated sample to determine a lipid transfer protein activity value; and,
   (d) comparing the sample's lipid transfer protein activity value to a predetermined standard value.

10. The method of claim 9 in which the lipid transfer protein is selected from the group consisting of CETP and MTP.

11. A non-radioactive method of determining the efficacy of a compound inhibiting lipid transfer protein activity comprising the steps of:
    (a) obtaining a sample of plasma from a mammal having a source of lipid transfer protein;
    (b) incubating for an effective time period the sample in a non-radioactive lipid transfer protein assay to obtain an incubated sample;
    (c) measuring fluorescent emission of lipid transfer protein activity of the incubated sample to determine a lipid transfer protein activity value; and,
    (d) comparing the sample's lipid transfer protein activity value to a predetermined standard value.

12. The method of claim 11 in which the compound inhibits the transcription of a gene coding for lipid transfer protein.

13. The method of claim 11 in which the compound inhibits the translation of a gene coding for lipid transfer protein.

14. The method of claim 11 in which the compound is a treatment for atherosclerosis.

15. A non-radioactive method of determining an HDL/LDL risk ratio comprising the steps of:
    (a) obtaining a CETP source from a donor;
    (b) incubating for an effective time period the CETP source in a non-radioactive CETP assay to obtain an incubated CETP source;
    (c) placing the incubated CETP source in a measurement instrument in which a value representing CETP activity for the source is obtained; and,
    (d) comparing the value representing CETP activity with a pre-determined range.

16. A non-radioactive method of assessing a medical condition correlated to lipid transfer activity comprising the steps:
    (a) obtaining a sample of plasma from a mammal having a source of lipid transfer protein;
    (b) incubating for an effective time period the sample in a non-radioactive lipid transfer protein assay to obtain an incubated sample;
    (c) measuring fluorescent emission of lipid transfer protein activity of the incubated sample to determine a lipid transfer protein activity value; and,
    (d) comparing the sample's lipid transfer protein activity value to a predetermined standard value.

17. The method of claim 16 in which the medical condition is hypoalphalipoproteinemia.

18. The method of claim 16 in which the medical condition is an abnormal ratio of plasma apolipoprotein A-I to apolipoprotein B ratio.

19. The method of claim 16 in which the medical condition includes risk factors for obesity.

20. The method of claim 16 in which the medical condition includes risk factors for diabetes.

21. The method of claim 16 further comprising the step of affecting CETP activity with a treatment.

22. The method of claim 16 in which the treatment is selected from the group consisting of a non-atherogenic diet modification regimen affecting physiological CETP activity, an inhibitor of CETP activity, and combinations thereof.

23. A non-radioactive method of screening for an inhibitor of a lipid transfer protein so that said inhibitor can be employed as an agent to regulate lipid transfer protein activity, comprising the steps of:
    (a) preparing a plurality of synthetic donor particle test solutions, the donor particles having a lipid derivative emitting electromagnetic radiation;
    (b) adding an acceptor particle to the test solutions for accepting the lipid derivative from the donor particle;
    (c) adding lipid transfer protein to the respective test solutions to shuttle the lipid derivative from the donor particle to the acceptor particles;
    (d) adding a prospective inhibitor of lipid transfer protein to the test solutions to obtain a group of prospective inhibitor containing test solutions;
    (e) incubating the prospective inhibitor test solutions;
    (f) measuring fluorescent emission of the activity of lipid transfer protein in prospective inhibitor containing test solutions; and,
    (g) isolating an effective inhibitor of lipid transfer protein activity from the group of prospective inhibitor containing test solutions.

24. The method of claim 23 further comprising the step of employing the effective inhibitor of lipid transfer protein as a therapeutic agent affecting lipid transfer protein activity.

25. The method of claim 23 in which the donor particle comprises NBD-triacylglycerol and derivatives thereof.

26. The method of claim 23 in which there is no separation of the donor particle and the acceptor particle after step (c).

27. The method of claim 23 in which the lipid transfer protein is a neutral lipid transfer protein.

28. The method of claim 27 in which the neutral lipid transfer protein is selected from the group consisting of CETP and MTP.

29. The method of claim 23 in which the inhibitor inhibits the transcription of a gene coding for CETP.

30. The method of claim 23 in which the compound inhibits the translation of a gene coding for CETP.

31. The method of claim 23 in which the compound is a treatment of atherosclerosis.

32. A well plate comprising a non-radioactive label emitting electromagnetic radiation at a wavelength other than a label emitting electromagnetic radiation used in an assay system disposed on the well plate.

33. An assay system for measuring the emission of electromagnetic radiation comprising a first reference label for determining the effect of spectral interference upon a second label.

34. A method of affecting lipid transfer protein activity comprising the step of administering a compound that modulates the entropic state of a transfer lipid that interacts with lipid transfer protein.

35. The method of claim 34 wherein the step of modulating comprises the step of administering a compound that affects the molecular alignment of constituents of the transfer lipid.

36. The method of claim 34 in which the step of modulating comprises the step of affecting the alignment of lipid molecules which comprise the transfer lipid substrate.

* * * * *